(12) United States Patent (10) Patent No.: US 7,910,319 B2
Wong et al. (45) Date of Patent: Mar. 22, 2011

(54) GLYCOPROTEOMIC PROBES FOR FLUORESCENT IMAGING FUCOSYLATED GLYCANS IN VIVO

(75) Inventors: Chi-Huey Wong, Taipei (TW); Tsui-Ling Hsu, Taipei (TW); Sarah R Hanson, San Marcos, CA (US); Masaaki Sawa, Ibaraki (JP)

(73) Assignee: Academia Sinica, Taipei (TW)

( * ) Notice: Subject to any disclaimer, the term of this patent is extended or adjusted under 35 U.S.C. 154(b) by 236 days.

(21) Appl. No.: 12/079,228

(22) Filed: Mar. 24, 2008

(65) Prior Publication Data

US 2008/0241856 A1 Oct. 2, 2008

Related U.S. Application Data

(60) Provisional application No. 60/896,787, filed on Mar. 23, 2007.

(51) Int. Cl.
*G01N 33/53* (2006.01)
(52) U.S. Cl. .......................................... 435/7.1; 436/87
(58) Field of Classification Search ........................ None
See application file for complete search history.

(56) References Cited

OTHER PUBLICATIONS

Hsu TL, Hanson SR, Kishikawa K, Wang SK, Sawa M, Wong CH, Alkynyl sugar analogs for the labeling and visualization of glycoconjugates in cells, (2007) Proc Natl Acad Sci 104:2614-2619.
Varki A, Cummings R, Esko JD, Freeze H, Hart GW, Marth J (1999) in Essentials of Glycobiology (Cold Spring Harbor Lab Press, Cold Spring Harbor, NY), pp. 1-635.
Axford JS, Glycosylation and rheumatic disease, (1999) Biochim Biophys Acta 1455:219-229.
Dube, D. H. & Bertozzi, C. R., Glycans in cancer and inflammation—potential for therapeutics and diagnostics, (2005) Nat. Rev. Drug Discov. 4, 477-488.
Mackiewicz A, Mackiewicz K, Glycoforms of serum a1-acid glycoprotein as markers of inflammation and cancer, (1995) Glycoconj J 12:241-247.
Meezan E, Wu HC, Black PH, Robbins PW, Comparative Studies on the Carbohydrate-Containing Membrane Components of Normal and Virus-Transformed Mouse Fibroblasts. II. Separation of Glycoproteins and Glycopeptides by Sephadex Chromatography*, (1969) Biochemistry 8:2518-2524.
Turner GA, N-Glycosylation of serum proteins in disease and its investigation using lectins, (1992) Clin Chim Acta 208:149-171.
Orntoft TF, Vestergaard EM, Clinical aspects of altered glycosylation of glycoproteins in cancer, (1999) Electrophoresis 20:362-371.
Sell S, Cancer-Associated Carbonhydrates Identified by Monoclonal Antibodies, (1990) Hum Pathol 21:1003-1019.
Taylor-Papadimitriou J, Epenetos AA, Exploiting altered glycosylation patterns in cancer: progress and challenges in diagnosis and therapy, (1994) Trends Biotechnol 12:227-233.
Zhang S, Cordon-Cardo C, Zhang HS, Reuter VE, Adluri S, Hamilton WB, Lloyd KO, Livingston PO, Selection of tumor antigens as targets for immune attack using immunohistochemistry: I. Focus on gangliosides, (1997) Int J Cancer 73:42-49.
Zhang S, Zhang HS, Cordon-Cardo C, Reuter VE, Singhal AK, Lloyd KO, Livingston PO, Selection of tumor antigens as targets for immune attack using immunohistochemistry: II. Blood group-related antigens, (1997) Int J Cancer 73:50-56.
Mahal LK, Yarema KJ, Bertozzi CR, Engineering Chemical Reactivity on Cell Surfaces Through Oligosaccharide Biosynthesis, (1997) Science 276:1125-1128.
Tai HC, Khidekel N, Ficarro SB, Peters EC, Hsieh-Wilson LC, Parallel Identification of O-GlcNAc-Modified Proteins from Cell Lysates, (2004) J Am Chem Soc 126:10500-10501.
Saxon E, Bertozzi CR, Cell Surface Engineering by a Modified Staudinger Reaction, (2000) Science 287:2007-2010.
Sampathkumar SG, Li AV, Jones MB, Sun Z, Yarema KJ, Metabolic installation of thiols into sialic acis modulates adhesion and stem cell biology, (2006) Nat Chem Biol 2:149-152.
Agard NJ, Baskin JM, Prescher JA, Lo A, Bertozzi CR, A Comparative Study of Bioorthogonal Reactions with Azides, (2006) ACS Chem Biol 1:644-648.
Agard NJ, Prescher JA, Bertozzi CR, A Strain-Promoted [3+2] Azide-Alkyne Cycloaddition for Covalent Modification of Biomolecules in Living Systems, (2004) J Am Chem Soc 126:15046-15047.
Rabuka D, Hubbard SC, Laughlin ST, Argade SP, Bertozzi CR, A Chemical Reporter Strategy to Probe Glycoprotein Fucosylation, (2006) J Am Chem Soc 128:12078-12079.
Sawa M., Hsu T. L., Itoh T., Sugiyama M., Hanson S. R., Vogt P. K., Wong C. H., Glycoproteomic probes for fluorescent imaging of fucosylated glycansin vivo, (2006) Proc. Natl. Acad. Sci. USA 103, 12371-12376.
Dube DH, Prescher JA, Quang CN, Bertozzi CR, Probing mucin-type O-linked glycosylation in living animals, (2006) Proc Natl Acad Sci USA 103:4819-4824.
Hang HC, Yu C, Kato DL, Bertozzi CR, A metabolic labeling approach toward proteomic analysis of mucin-type O-linked glycosylation, (2003) Proc Natl Acad Sci USA 100:14846-14851.
Becker, D. J. & Lowe, J. B., Fucose: biosynthesis and biological function in mammals, (2003) Glycobiology 13, 41R-53R.
Keppler OT, Horstkorte R, Pawlita M, Schmidt C, Reutter W, Fucose: biosynthesis and biological function in mammals, (2001) Glycobiology 11:11R-18R.

(Continued)

*Primary Examiner* — Jacob Cheu
(74) *Attorney, Agent, or Firm* — Eckman Basu LLP

(57) ABSTRACT

The disclosure provides a method of labeling of cellular glycans bearing azide groups via a fluorescent labeling technique based on Cu(I)-catalyzed [3+2]cycloaddition (click activation) of a probe comprising an alkynyl group. The method entails generating a fluorescent probe from a nonfluorescent precursor, 4-ethynyl-N-ethyl-1,8-naphthalimide, by Cu(I)-catalyzed [3+2]cycloaddition of the alkyne group of the probe with an azido-modified sugar. The disclosure further provides a method of incorporating an azido-containing fucose analog into glycoconjugates via the fucose salvage pathway. The disclosure provides a method of fluorescent visualization of fucosylated cells by flow cytometry when cells treated with 6-azidofucose are labeled with the click-activated fluorogenic probe or biotinylated alkyne. A method of visualizing the intracellular localization of fucosylated glycoconjugates by fluorescence microscopy is also disclosed.

9 Claims, 12 Drawing Sheets

OTHER PUBLICATIONS

Rostovtsev VV, Green LG, Fokin VV, Sharpless KB, A Stepwise Huisgen Cycloaddition Process: Copper(I)-Catalyzed Regioselective "Ligation" of Azides and Terminal Alkynes**, (2002) Angew Chem Int Ed Engl 41:2596-2599.

Wang Q, Chan TR, Hilgraf R, Fokin VV, Sharpless KB, Finn MG, Bioconjugation by Copper(I)-Catalyzed Azide-Alkyne [3+2] Cycloaddition, (2003) J Am Chem Soc 125:3192-3193.

Jacobs CL, Yarema KJ, Mahal LK, Nauman DA, Charters NW, Bertozzi CR, Metabolic Labeling of Glycoproteins with Chemical Tags through Unnatural Sialic Acid Biosynthesis, (2000) Methods Enzymol 327:260-275.

Sarkar AK, Fritz TA, Taylor WH, Esko JD, Disaccharide uptake and priming in animal cells: Inhibition of sialyl Lewis Xby acetylated Galll1-4GlcNAcl3- Onaphthalenemethanol, (1995) Proc Natl Acad Sci USA 92:3323-3327.

Sivakumar K, Xie F, Cash BM, Long S, Barnhill HN, Wang Q, A Fluorogenic 1,3-Dipolar Cycloaddition Reaction of 3-Azidocoumarins and Acetylenes, (2004) Org Lett 6:4603-4606.

Yarema KJ, Mahal LK, Bruehl RE, Rodriguez EC, Bertozzi CR, Metabolic Delivery of Ketone Groups to Sialic Acid Residues, (1998) J Biol Chem 273:31168-31179.

Speers AE, Cravatt BF, Profiling Enzyme Activities In Vivo Using Click Chemistry Methods, (2004) Chem Biol 11:535-546.

Hanson S, Best M, Bryan MC, Wong CH, Chemoenzymatic synthesis of oligosaccharides and glycoproteins (2004) Trends Biochem Sci 29:656-663.

Luchansky SJ, Bertozzi CR, Azido Sialic Acids Can Modulate Cell-Surface Interactions, (2004) Chembiochem 5:1706-1709.

Fujihashi M, Peapus DH, Kamiya N, Nagata Y, Miki K, Crystal Structure of Fucose-Specific Lectin from *Aleuria aurantia* Binding Ligands at Three of Its Five Sugar Recognition Sites, (2003) Biochemistry 42:11093-11099.

Wimmerova M, Mitchell E, Sanchez JF, Gautier C, Imberty A, Crystal Structure of Fungal Lectin, (2003) J Biol Chem 278:27059-27067.

Simanek EE, McGarvey GJ, Jablonowski JA, Wong CH, Selectin-Carbohydrate Interactions: From Natural Ligands to Designed Mimics, (1998) Chem Rev 98:833-862.

Yang L, McRae R, Henary MM, Patel R, Lai B, Vogt S, Fahrni CJ, Imaging of the intracellular topography of copper with a fluorescent sensor and by synchrotron x-ray fluorescence microscopy, (2005) Proc Natl Acad Sci USA 102:11179-11184.

Apweiler, R., Hermjakob, H. & Sharon, N., On the frequency of protein glycosylation, as deduced from analysis of the SWISS-PROT database, (1999) Biochim. Biophys. Acta 1473, 4-8.

Staudacher, E., α 1,3-Fucosyltransferases, (1996) Trends Glycosci. Glycotechnol. 8, 391-408.

Sears, P. & Wong, C.-H., Enzyme action in glycoprotein synthesis, (1998) Cell. Mol. Life Sci. 54, 223-252.

Haltiwanger, R. S. & Lowe, J. B., Role of glycosylation in development, (2004) Annu. Rev. Biochem. 73, 491-537.

Hirabayashi, J., Lectin-based structural glycomics: Glycoproteomics and glycan profiling, (2004) Glycoconj. J. 21, 35-40.

Shriver, Z., Raguram, S. & Sasisekharan, R., Glycomics: a pathway to a class of new and improved therapeutics, (2004) Nat. Rev. Drug Discov. 3, 863-873.

Khidekel, N., Ficarro, S. B., Peters, E. C. & Hsieh-Wilson, L. C., Exploring the O-GlcNAc proteome: Direct identification of O-GlcNAc-modified proteins from the brain, (2004) Proc. Natl. Acad. Sci. USA 101, 13132-13137.

Ratner, D. M., Adams, E. W., Disney, M. D. & Seeberger, P. H., Tools for Glycomics: Mapping Interactions of Carbohydrates in Biological Systems, (2004) ChemBioChem 5, 1375-1383.

Prescher, J. A. & Bertozzi, C. R., Chemistry in living systems, (2005) Nat. Chem. Biol. 1, 13-21.

Raman, R., Raguram, S., Venkataraman, G., Paulson, J. C. & Sasisekharan, R., Glycomics: an integrated systems approach to structure-function relationships of glycans, (2005) Nat. Methods 2, 817-824.

Chudakov, D. M., Lukyanov, S. & Lukyanov, K. A., Fluorescent proteins as a toolkit for in vivo imaging, (2005) Trends Biotechnol. 23, 605-613.

Kolb, H. C. & Sharpless, K. B., The growing impact of click chemistry on drug discovery, (2003) Drug Discov. Today 8, 1128-1137.

Zhou, Z. & Fahrni, C. J., A Fluorogenic Probe for the Copper(I)-Catalyzed Azide-Alkyne Ligation Reaction: Modulation of the Fluorescence Emission via 3 (n,δ*)-1(δ,δ*) Inversion, (2004) J. Am. Chem. Soc. 126, 8862-8863.

de Silva, A. P., Gunaratne, H. Q. N. & Gunnlaugsson, T., Flourescent PET(Photoinduced Electron Transfer) Reagents for Thiols, (1998) Tetrahedron Lett. 39, 5077-5080.

McAdam, C. J., Morgan, J. L., Murray, R. E., Robinson, B. H. & Simpson, J., Synthesis and Flourescence Properties of New Enaminenaphthalimides, (2004) Aust. J. Chem. 57, 525-530.

Tonetti, M., Sturla, L., Bisso, A., Zanardi, D., Benatti, U. & De Flora, A., The metabolism of 6-deoxyhexoses in bacterial and animal cells, (1998) Biochimie 80, 923-931.

Zeitler, R., Danneschewski, S., Lindhorst, T., Thiem, J. & Reutter, W., Inhibition of L-fucokinase from rat liver by L-fucose analogues in vitro, (1997) J. Enzyme Inhib. 11, 265-273.

Yurcheno, P. D. & Atkinson, P. H., Fucosyl-Glycoprotein and Precursor Pools in HeLa Cells, (1975) Biochemistry 14, 3107-3114.

Yurcheno, P. D. & Atkinson, P. H., Equilibration of Fucosyl Glycoprotein Pools in HeLa Cells, (1977) Biochemistry 14, 944-953.

Dube, D. H. & Bertozzi, C. R., Metabolic oligosaccharide engineering as a tool for glycobiology, (2003) Curr. Opin. Chem. Biol. 7, 616-625.

Düffels, A., Green, L. G., Lenz, R., Ley, S. V., Vincent, S. P. & Wong, C.-H., Chemoenzymatic Synthesis of L-Galactosylated Dimeric Sialyl Lewis X Structures Employing -1,3-Fucosyltransferase V, (2000) Bioorg. Med. Chem. 8, 2519-2525.

Srivastava, G., Kaur, K. J., Hindsgaul, O. & Palcic, M. M., Enzymatic Transfer of a Preassembled Trisaccharide Antigen to Cell Surfaces Using a Fucosyltransferase, (1992) J. Biol. Chem. 267, 22356-22361.

Vogel, C., Bergemann, C., Ott, A.-J., Lindhorst, T. K., Thiem, J., Dahlhoff, W. V., Hällgren C., Palcic, M. M. & Hindsgaul, O., Synthesis of Carbon-Backbone-Elongated GDP-L-Fucose Derivatives as Substartes for Fucosyltransferase-Catalysed Reactions, (1997) Liebigs Ann. 601-612.

Binch, H., Stangier, K. & Thiem, J., Chemical synthesis of GDP-L-galactose and analogues, (1998) Carbohydr. Res. 306, 409-419.

Gilbert, J. C. & Weerasooriya, U., Diazoethenes: their attempted synthesis from akehydes and aromatic ketones by way of the Horner-Emmons modification of the Wittig reaction. A facile synthesis of Alkynes1-3, (1982) J. Org. Chem. 47, 1837-1845.

Huisgen, R., 1,3-Dipolar Cycloadditions Past and Future, (1963) Angew. Chem. Int. Ed. Engl. 2, 565-632.

Chan, T. R., Hilgraf, R., Sharpless, K. B. & Fokin, V. V., Polytriazoles as Copper(I)-Stabilizing Ligands in Catalysis, (2004) Org. Lett. 6, 2853-2855.

Lewis, W. G., Magallon, F. G., Fokin, V. V. & Finn, M. G., Discovery and Characterization of Catalysts for Azide-Alkyne Cycloaddition by Fluorescence Quenching, (2004) J. Am. Chem. Soc. 126, 9152-9153.

Wittmann, V. & Wong, C.-H., 1H-Tetrazole as Catalyst in Phosphomorpholidate Coupling Reactions: Efficient Synthesis of GDP-Fucose, GDP-Mannose, and UDP-Galactose, (1997) J. Org. Chem. 62, 2144-2147.

Fazio, F., Bryan, M. C., Blixt, O., Paulson, J. C. & Wong, C.-H., Synthesis of Sugar Arrays in Microtiter Plate, (2002) J. Am. Chem. Soc. 124, 14397-14402.

Bryan, M. C., Lee, L. V. & Wong, C.-H., High-throughput identification of fucosyltransferase inhibitors using carbohydrate microarrays, (2004) Bioorg. Med. Chem. Lett. 14, 3185-3188.

Rydeń, I., Påhlsson, P. & Lindgren, S., Diagnostic Accuracy of a1-Acid Glycoprotein Fucosylation for Liver Cirrhosis in Patients Undergoing Hepatic Biopsy, (2002) Clin. Chem. 48, 2195-2201.

Hashimoto, S., Asao, T., Takahashi, J., Yagihashi, Y., Nishimura, T., Saniabadi, A. R., Poland, D. C., van Dijk, W., Kuwano, H., Kochibe, N. & Yazawa, S., a1-Acid Glycoprotein Fucosylation as a Marker of Carcinoma Progression and Prognosis, (2004) Cancer 101, 2825-2836.

Link, A. J. Vink, M. K. S. & Tirrell, D. A., Presentation and Detection of Azide Functionality in Bacterial Cell Surface Proteins, (2004) J. Am. Chem. Soc. 126, 10598-10602.

Walz, G., Aruffo, A., Kolanus, W., Bevilacqua, M. & Seed, B., Recognition by ELAM-1 of the Sialyl-Lex Determinant on Myeloid and Tumor Cells, (1990) Science 250, 1132-1135.

Taniguchi, N., Ekuni, A., Ko, J. H., Miyoshi, E., Ikeda, Y., Ihara, Y., Nishikawa, A., Honke, K. & Takahashi, M., A glycomic approach to the identification and characterization of glycoprotein function in cells transfected with glycosyltransferase genes, (2001) Proteomics 1, 239-247.

Kannagi, R., Izawa, M., Koike, T., Miyazaki, K. & Kimura, N., Carbohydrate-mediated cell adhesion in cancer metastasis and angiogenesis, (2004) Cancer Sci. 95, 377-384.

Miyoshi, E., Noda, K., Yamaguchi, Y., Inoue, S., Ikeda, Y., Wang, W., Ko, J. H., Uozumi, N., Li, W. & Taniguchi, N., The a1-6-fucosyltransferase gene and its biological significance, (1999) Biochim. Biophys. Acta 1473, 9-20.

Hakomori, S. & Zhang, Y., Glycosphingolipid antigens and cancer therapy, (1997) Chem. Biol. 4, 97-104.

Kannagi, R., Levery, S. B., Ishigami, F., Hakomori, S. I., Shevinsky, L. H., Knowles, B. B. & Solter, D., New Globoseries Glycosphingolipids in Human Teratocarcinoma Reactive with the Monoclonal Antibody Directed to a Developmentally Regulated Antigen, Stage-specific Embryonic Antigen 3, (1983) J. Biol. Chem. 258, 8934-8942.

Huang, C.-Y., Thayer, D. A., Chang, A. Y., Best, M. D., Hoffmann, J., Head, S. & Wong, C.-H., Carbohydrate microarray for profiling the antibodies interacting with Globo H tumor antigen, (2006) Proc. Natl. Acad. Sci. USA 103, 15-20.

Schottelius, A. J., Hamann, A. & Asadullah, K., Role of fucosyltransferases in leukocyte trafficking: major impact for cutaneous immunity, (2003) Trends Immunol. 24, 101-104.

Javaud, C., Dupuy, F., Maftah, A., Julien, R. & Petit, J. M., The fucosyltransferase gene family: an amazing summary of the underlying mechanisms of gene evolution, (2003) Genetica 118, 157-170.

Roos, C., Kolmer, M., Mattila, P. & Renkonen, R., Composition of *Drosophila melanogaster* Proteome Involved in Fucosylated Glycan Metabolism, (2002) J. Biol. Chem. 277, 3168-3175.

Baboval, T. & Smith, F. I., Compatison of human and mouse Fuc-TX and Fuc-TXI genes, and expression studies in the mouse, (2002) Mamm. Genome 13, 538-541.

Oriol, R., Mollicone, R., Cailleau, A., Balanzino, L. & Breton, C., Divergent evolution of fucosyltransferase genes from vertebrates, invertebrates, and bacteria, (1999) Glycobiology 9, 323-334.

Staudacher, E., Altmann, F., Wilson, I. B. H. & März, L., Fucose in N-glycans: from plant to man, (1999) Biochim. Biophys. Acta 1473, 216-236.

Piller, V., Piller, F. & Fukuda, M., Biosynthesis of Truncated 0-Glycans in the T Cell Line Jurkat, (1990) J. Biol. Chem. 265, 9264-9271.

Mitchell, M. L., Tian, F., Lee, L. V. & Wong, C.-H., Synthesis and Evaluation of Transition-State Analogue Ingibitors of a-1,3-Fucosyltransferase, (2002), Angew. Chem. Int. Ed. Engl. 41, 3041-3044.

Lee, L. V., Mitchell, M. L., Huang, S.-J., Fokin, V. V., Sharpless, K. B. & Wong, C.-H., A Potent and Highly Selective Inhibitor of Human r-1,3-Fucosyltransferase via Click Chemistry, (2003) J. Am. Chem. Soc. 125, 9588-9589.

Hanson S. R., Hsu T. L., Weerapana E., Kishikawa K., Simon G. M., Cravatt B. F., Wong C. H., Tailored glycoproteomics and glycan site mapping using saccharide-selective bioorthogonal probes (2007) J Am Chem Soc. 129, 7266-7267.

Lowe, JB; Marth, JD., A Genetic Approach to Mammalian Glycan Funciton, Annu Rev Biochem. 2003;72:643-91.

Sears, P; Wong, CH. Toward Automated Synthesis of Oligosaccharides and Glycoproteins, Science. 2001;291:2344-50.

Grogan, MJ; Hanson, S; Best, M; Bryan, MC; Wong, CH., Chemoenzymatic synthesis of oligosaccharides and glycoproteins, Trend Biochem Sci. 2004;29:656-63.

Brik, A; Ficht, S; Wong, CH. Strategies for the preparation of homogenous glycoproteins, Cur Opin Chem Biol. 2006;10:638-44.

Bond, MR; Kohler, JJ. Chemical methods for glycoprotein discovery, Curr Opin Chem Biol. 2007;11:52-8.

Morelle, W; Canis, K; Chirat, F; Faid, V; Michalski, JC. The use of mass spectrometry for the proteomic analysis of glycosylation, Proteomics. 2006;6:3993-4015.

Prescher, JA; Bertozzi, CR. Chemical Technologies for Probing Glycans, Cell. 2006;126:851-854.

Laughlin, ST; Agard, NJ; Baskin, JM; Carrico, IS; Chang, PV; Ganguli, AS; Hangauer, MJ; Lo, A; Prescher, JA; Bertozzi, CR; Minoru, F., Metabolic Labeling of Glycans with Azido Sugars for Visualization and Glycoproteometics, Meth Enzym. vol. 415. Academic Press; 2006. pp. 230-250.

Speers, AE; Cravatt, BF., A Tandem Orthogonal Proteolysis Strategy for High-Content Chemical Proteomics, J Am Chem Soc. 2005;127:10018-9.

Zhang, H; Li, XJ; Martin, DB; Aebersold, R., A Tandem Orthogonal Proteolysis Strategy for High-Content Chemical Proteomics, Nat Biotech. 2003;21:660-6.

Kaji, H; Saito, H; Yamauchi, Y; Shinkawa, T; Taoka, M; Hirabayashi, J; Kasai, K; Takahashi, N; Isobe, T., A Tandem Orthogonal Proteolysis Strategy for High-Content Chemical Proteomics, Nat Biotech. 2003;21:667-72.

Kaji, H; Isobe, T., Large-Scale Analysis of Glycoproteins by LC-MS Method, Trend Glycosci Glycotech. 2006;18:313-22.

Eng, JK; McCormack, AL; Yates, JR., An approach to correlate tandem mass spectral data of peptides with amino acid sequences in a protein database, J Amer Soc Mass Spec. 1994;5:976-89.

Washburn, MP; Wolters, D; Yates, JR., Large-scale analysis of the yeast proteome by multidimensional protein identification technology, 3rd Nat Biotech. 2001;19:242-7.

Lewandrowski, U; Moebius, J; Walter, U; Sickmann, A., Elucidation of N-Glycosylation Sites on Human Platelet Proteins, Mol Cell Proteomics. 2006;5:226.

Ramachandran, P; Boontheung, P; Xie, Ym; Sondej, M; Wong, DT; Loo, JA., Identification of N-Linked Glycoproteins in Human Saliva by Glycoprotein Capture and Mass Spectrometry, J Proteome Res. 2006;5:1493.

Liu, T; Qian, WJ; Gritsenko, MA; Campli, DG; Monroe, ME; Moore, RJ; Smith, RD., Human Plasma N-Glycoproteome Analysis by Immunoaffinity Subtraction, Hydrazide Chemistry, and Mass Spectrometry, J Prot Res. 2005;4:2070.

Roth, J., Protein N-Glycosylation along the Secretory Pathway: Relationship to Organelle Topography and Function, Protein Quality Control, and Cell Interactions, Chem Rev. 2002;102:285-304.

Shiraki, K; Takase, K; Tameda, Y; Hamada, M; Kosaka, Y; Nakano, T., A clinical study of lectin-reactive alpha-fetoprotein as an early indicator of hepatocellular carcinoma in the follow-upof cirrhotic patients, Hepatology. 1995;22:802-7.

Comunale, MA; Lowman, M; Long, RE; Krakover, J; Philip, R; Seeholzer, S; Evans, AA; Hann, HWL; Block, TM; Mehta, AS., Proteomic analysis of serum associated fucosylated glycoproteins in the development of primary hepatocellular carcinoma, J Proteome Res. 2006;5:3108-15.

Wells, L; Vosseller, K; Cole, RN; Cronshaw, JM; Matunis, MJ; Hart, GW., Mapping Sites of O-GlcNAc Modification Using Affinity Tags for Serine and Threonine Post-translational Modifications, Mol Cell Proteomics. 2002;1:791-804.

Vosseller, K; Trinidad, JC; Chalkley, RJ; Specht, CG; Thalhammer, A; Lynn, AJ; Snedecor, JO; Guan, S; Medzihradszky, KF; Maltby, DA; Schoepfer, R; Burlingame, AL., O-Linked N-Acetylglucosamine Proteomics of Postsynaptic Density Preparations Using Lectin Weak Affinity Chromatography and Mass Spectrometry, Mol Cell Proteomics. 2006;5:923-34.

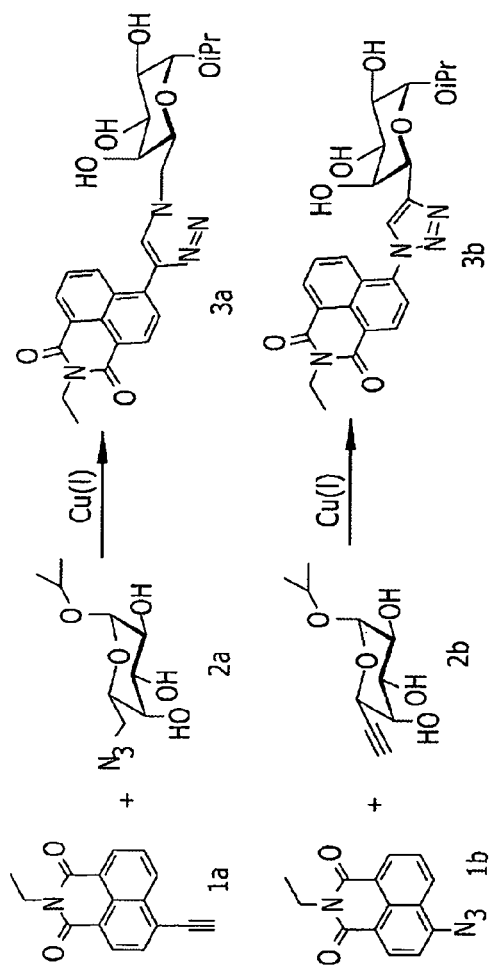
FIG. 3A
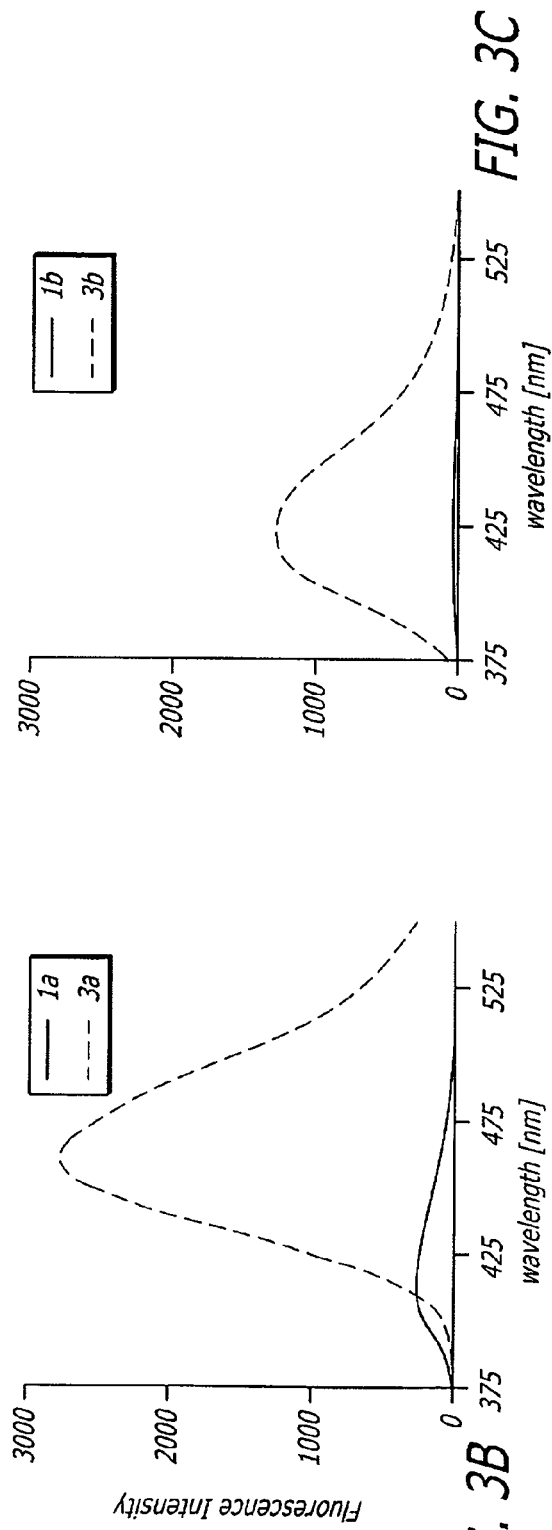
FIG. 3B
FIG. 3C

8: R= —≡
9: R= —CH₂N₃
10: R= Me

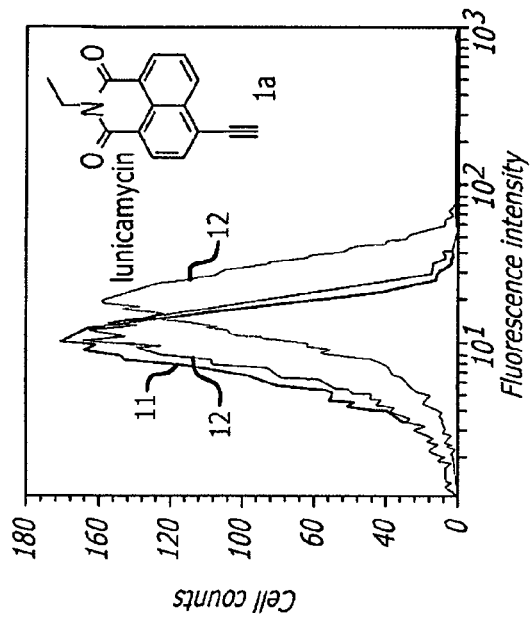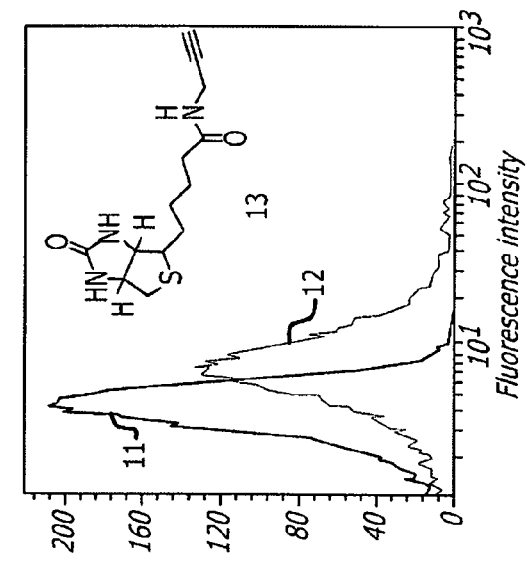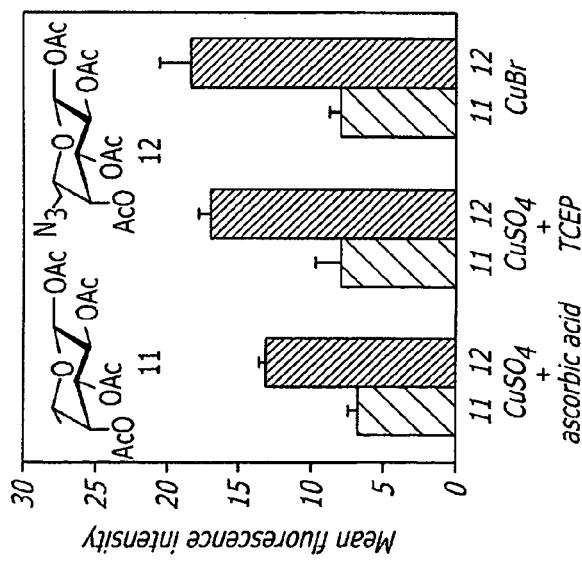
FIG. 5B
FIG. 5C
FIG. 5A

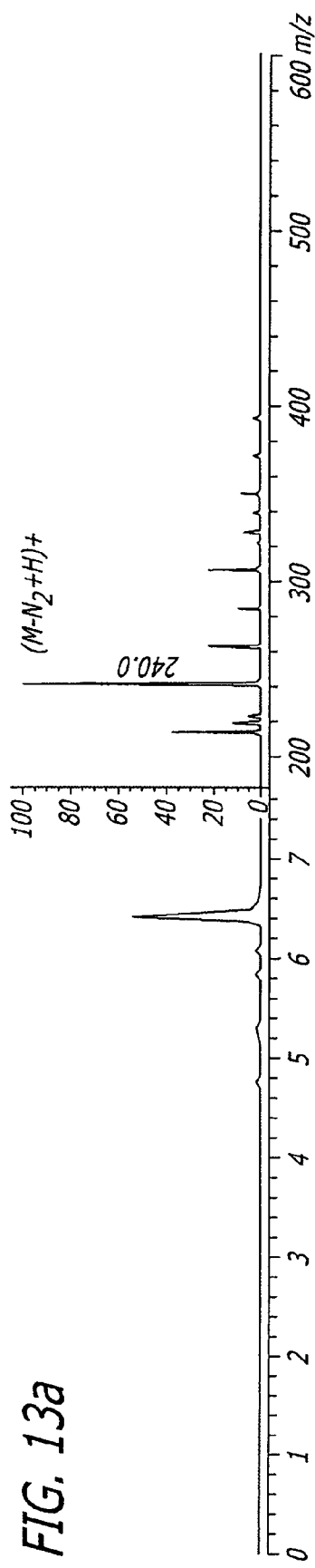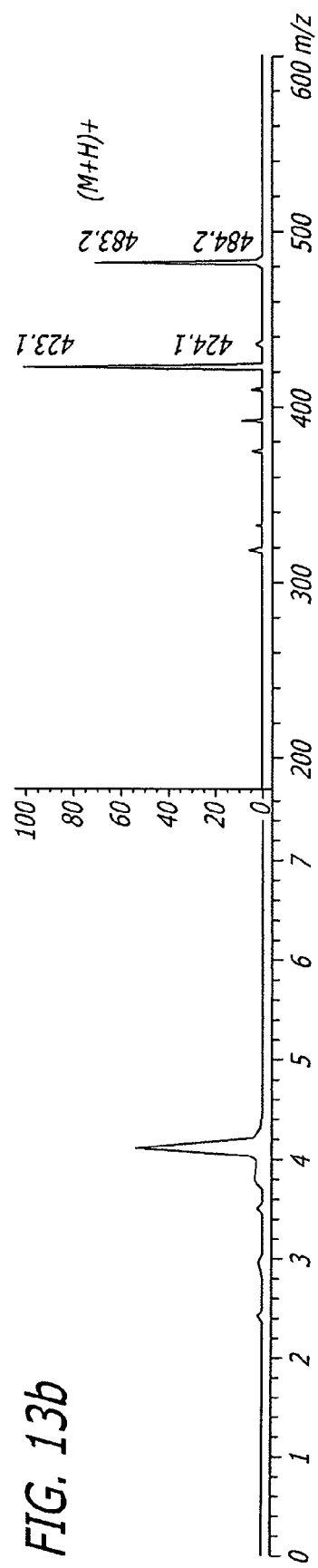
FIG. 13a
FIG. 13b

GLYCOPROTEOMIC PROBES FOR FLUORESCENT IMAGING FUCOSYLATED GLYCANS IN VIVO

RELATED APPLICATIONS

This disclosure claims the Paris Convention Priority of U.S. Provisional Patent Application Ser. No. 60/896,787, entitled "Provisional patent application for Pro-Glycoproteomic Probes for Fluorescent Imaging of Fucosylated Glycans in vivo" filed Mar. 23, 2007, the contents of which are incorporated by reference as if fully disclosed herein.

GOVERNMENT DISCLOSURE

This research was supported by the National Institutes of Health and The Skaggs Institute for Chemical Biology.

FIELD OF THE DISCLOSURE

The disclosure provides a method of fluorescent labeling of cellular glycans bearing azide groups based on Cu(I)-catalyzed [3+2] azide-alkyne cycloaddition (CuAAC) of a probe comprising an alkynyl group. The disclosure also provides a method of incorporating a derivatized fucose analog into a cellular glycoconjugate via the fucose salvage pathway. The disclosure further provides a method of fluorescent visualization of fucosylated cells by flow cytometry and a method of visualizing the intracellular localization of fucosylated glycoconjugates by fluorescence microscopy.

BACKGROUND

Glycans are integral components of biological systems with far reaching activities, many of which are only beginning to be understood. Glycans constitute the most abundant and diverse class of biomolecules found in natural systems, consisting of oligosaccharide chains that are present as independent polysaccharides (e.g., cellulose, an important structural component in plants; and heparin sulfate, an import factor of blood clotting in mammals) or as glycoconjugates with lipids (glycolipids), proteins (glycoproteins, proteoglycans), and small molecule natural products (e.g., antibiotics such as erythromycin, vancomycin, and teicoplanin).

Glycans play a role in almost every aspect of cellular activity. Most glycans in higher eukaryotes are produced in the secretory pathway by glycosylation events, which entail the enzymatic transfer of saccharides or oligosaccharide chains onto lipids and proteins. Protein glycosylation is a complex co- or post-translational process that modifies the majority of the human proteome and serves a vast array of biological functions. Protein glycosylation exerts intrinsic effects on structure, from mediating folding and oligimerization, to increasing stability, solubility, and circulation time. Inside of the cell, glycans affect recognition, binding, targeting, and cellular distribution. At the cell surface, glycans are prominently displayed where they are involved in a host of molecular recognition events that modulate important physiological processes, such as cell-cell adhesion, inflammation, angiogenesis, coagulation, embryogenesis, differentiation, communication, and a myriad of other cellular signaling pathways.

Cell surface glycans have also been associated with physiological dysfunctions such as bacterial and viral infection, rheumatoid arthritis, and tumor progression. In the latter case, several types of oncofetal and aberrant glycans have been established to correlate with malignancy, invasiveness, inflammation and cancer metastasis. In particular, altered terminal fucosylation and sialylation, which are believed to result from changes in expression locations and levels of fucosyltransferases (an enzyme that transfers a fucose from a donor substrate to an acceptor substrate, a glycoconjugate or glycan) and sialyltransferases (an enzyme that transfers a sialic acid from a donor substrate to an acceptor substrate, a glycoconjugate or glycan) respectively, are associated with tumor malignancy. For example, glycan determinants like Lewis y, Lewis x, sialyl Lewis x, sialyl Lewis a, sialyl Tn, Globo H, fucosyl GM1, and polysialic acid are expressed at elevated levels in neoplastic tissues. For this reason, these epitopes are promising and eagerly pursued targets for glycan-based vaccines. Additionally, several congenital glycosylation disorders, lysosomal storage disorders, and immunological diseases have been linked with dysregulation of glycan catabolism/metabolism. Although known to be involved in physiological and pathophysiological events, the identification of many glycan structures and delineation of their mode of action at the molecular level has been complicated by their underpinning complexity.

Glycan complexity results from many factors. They are synthesized in a non-templated, post-translational process, which means that sites of glycoconjugate glycosylation and structures within them have proven, thus far, to be minimally predicatable. This also means that glycans cannot be genetically manipulated in a similar fashion to DNA and proteins. Glycans are synthesized in the secretory pathway by a suite of enzymes that are subject to multifaceted controls. The end glycan products can have enormous structural complexity (many possible glycan structures, the diversity of which is also a function of the sugar building blocks), structural microheterogeneity (multiple different glycan structures attached to a glycoconjugate at the same position), and structural macro-heterogeneity (multiple sites and types of glycan attachment; for example, glycoproteins can be N-linked at Asn residues, or O-linked at Ser/Thr resides). Heterogeneity in glycan structures appears to be dynamically regulated and functionally significant, governing multivalent interactions the cell surface. Heterogeneity and multivalency complicate structure-function studies and the isolation of homogenous glycans in meaningful amounts from natural sources is nearly impossible. For the procurement of homogenous glycoconjugates/glycans synthesis is the only viable route, but remains one of the most formidable challenges in glycobiology.

The link between glycan activity and complexity has presented major challenges to deciphering their activities on an individual protein, let alone, proteomic scale. Among the challenges facing global analysis are development of general methods for isolating glycans from complex proteomes; determining saccharide composition, site of protein modification, and fraction occupancy; and understanding the direct roles of glycans in cellular function and dysfunction.

Specific glycan-tagging systems provide a powerful method for probing the structure of heterogeneous glycans. The key to glycan tagging entails incorporating modified sugars derivatized with chemical reporting groups into cellular glycans (typically via the normal biosynthetic pathways, a process known as metabolic oligosaccharide engineering, or MOE) and then detecting the tagged-glicans by labeling their chemical reporting groups with a complementary probe that chemically reacts with them in a specific manner. Many selective chemical probing techniques have been used for performing chemistry with chemical reporting group-tagged glycoconjugates in cells. These methods include bioorthogonal reactions such as ketoneaminooxy/hydrazide ligation, Staudinger ligation, Michael addition, and the strain-promoted, and Cu(I)-catalyzed [3+2] azide-alkyne cycloaddition (CuAAC). Several chemical reporting groups are tolerated and successfully incorporated into glycoconjugates using MOE, including ketones, thiols, photoreactive groups, azides, and alkynes. These reporting sugars have been labeled with tags such as FLAG peptides, biotin, and fluorescent or fluorogenic molecules. The strength of these systems is that the labeled glycan products have the potential to be manipulated for specific glycan studies involving: enrichment and glycoproteomic analysis by means of mass spectrometry detection and/or quantitation by flow cytometry or visualization through microscopy to obtain information about glycan localization, trafficking, and dynamics.

The incorporation of exogenous natural or unnatural sugars into glycans has been achieved by cellular biosynthetic pathways. These processes involve multistep enzymatic transformations that render free sugars in the cytosol into nucleotide-donor sugars, the substrates for glycosyltransferases. In the case of fucose (Fuc), a salvage pathway consisting of Fuc kinase and GDP-Fuc (guanosine diphosphate fucose) pyrophosphorylase contributes to the production of GDP-Fuc, which is then exploited by fucosyltransferases (FucTs) located in the Golgi apparatus to add Fuc onto glycoconjugates. Modifications at the 6-position of Fuc are tolerated by the salvage pathway and FucTs. In the sialic acid (NeuAc) biosynthetic pathway, the precursor N-acetylmannosamine (ManNAc) is derived from GlcNAc or UDP-GlcNAc through specific epimerases, then sequentially converted to sialic acid by the cytosolic enzymes ManNAc 6-kinase, sialic acid-9-phosphate synthase, and sialic acid-9-phosphate phosphatase. CMP-NeuAc is subsequently formed in the nucleus, and transported to the Golgi apparatus for glycan elaboration by sialyltransferases. Studies on metabolic delivery of mannosamine or ManNAc analogs show that N-acyl chains up to five carbon atoms long are tolerated by the sialic acid biosynthetic pathway.

The incorporation of exogenous natural or unnatural sugars comprising less toxic probes into glycans by cellular biosynthetic pathways is would be important to the study of glycosylation is likely to provide useful information for diagnosis and disease prognosis, in addition to unveiling new therapeutic targets.

SUMMARY

Herein disclosed is a fluorescent labeling method based on CuAAC, or click chemistry, which allows rapid, versatile, and specific covalent labeling of cellular glycans bearing azide groups. The method entails generating a fluorescent probe from a nonfluorescent precursor, 4-ethynyl-N-ethyl-1,8-naphthalimide, by clicking the fluorescent trigger, the alkyne at the 4 position, with an azido-modified sugar. Using this click-activated fluorescent probe, incorporation of an azido-containing fucose analog into glycoconjugates via the fucose salvage pathway is disclosed. It is further disclosed that this click-activated fluorogenic labeling technique is sufficiently sensitive and selective to visualize fucosylated glycoconjugates in whole cells.

Distinct fluorescent signals are observed by flow cytometry when cells treated with 6-azidofucose are labeled with the click-activated fluorogenic probe or biotinylated alkyne. The intracellular localization of fucosylated glycoconjugates is visualized by using fluorescence microscopy. This technique allows dynamic imaging of cellular fucosylation and facilitates studies of fucosylated glycoproteins and glycolipids.

In one aspect, the disclosure provides a method of labeling a glycoconjugate, the method comprising: incubating an azido-derivatized fucose-GDP analog with a glycoconjugate and a fucosyltransferase to create an azido-derivatized glycoconjugate; and contacting the azido-derivatized glycoconjugate with a chemical probe wherein said chemical probe reacts with said azido group in the azido-derivatized glycoconjugate to create a labeled glycoconjugate.

In one aspect, the azido-derivatized glycoconjugate is a fucosylated glycoconjugate. In another aspect, the labeled glycoconjugate is a fluorescently labeled glycoconjugate. In a further aspect, the azido-derivatized fucose-GDP analog is guanosine 5'-diphospho-6-azido-beta-L-fucopyranoside triethylammonium salt. In one aspect, the chemical probe comprises an alkynyl group. In another aspect, the chemical probe further comprises one of an N-alkyl-1,8-naphthalimide group, a biotin group, or a coumarin group. In a further aspect, the chemical probe is 4-ethynyl-N-ethyl-1,8-naphthalimide.

In one aspect, the disclosure provides a method of labeling a cellular glycoconjugate, the method comprising: incorporating an azido-derivatized fucose into a glycoconjugate in a cell by growing the cell in the presence of the azido-derivatized fucose to create an azido-derivatized glycoconjugate; and contacting the azido-derivatized glycoconjugate with a chemical probe wherein said chemical probe reacts with said azido-group in the azido-derivatized glycoconjugate to create a labeled glycoconjugate. In one aspect, the method further comprises permeabilizing the cell prior to the contacting step. In another aspect, the method further comprises extracting the cell prior to the contacting step. In a further aspect, the labeled glycoconjugate is a fluorescent labeled glycoconjugate. In another aspect, the chemical probe comprises an alkynyl group. In one aspect, the chemical probe further comprises one of an N-alkyl-1,8-naphthalimide group, a biotin group, or a coumarin group. In a specific aspect, the chemical probe is 4-ethynyl-N-ethyl-1,8-naphthalimide. In another aspect, the method further comprises detecting the labeled glycoconjugate by one or more techniques of flow cytometry, SDS-PAGE, Western blot, ELISA and confocal microscopy. In another aspect, the method further comprises quantifying the labeled-glycoconjugate by one or more techniques of flow cytometry, SDS-PAGE, Western blot, ELISA and confocal microscopy.

In one aspect, the disclosure provides a method of identifying a fucosylated glycoconjugate in a cell, the method comprising: incorporating an azido-derivatized fucose into a glycoconjugate in a cell by growing the cell in the presence of the azido-derivatized fucose to create an azido-derivatized fucosylated glycoconjugate; contacting the azido-derivatized fucosylated glycoconjugate to a chemical probe which will bind covalently to the azido group to create a labeled glycoconjugate; and detecting the labeled glycoconjugate to determine that the labeled glycoconjugate in the cell is a fucosylated glycoconjugate.

In another aspect, the disclosure provides a method of detecting an azido-derivatized glycan, the method comprising: contacting an azido-derivatized glycan with a chemical probe wherein said chemical probe reacts with said azido group in the azido-derivitized glycan to create a fluorescent labeled glycan; and detecting the fluorescent labeled glycan by one or more techniques of flow cytometry, SDS-PAGE, Western blot, ELISA and confocal microscopy. In one aspect the chemical probe comprises an alkynyl group. In another aspect, the chemical probe further comprises one of an N-alkyl-1,8-naphthalimide group, a biotin group, or a coumarin group. In a specific aspect, the chemical probe is 4-ethynyl-N-ethyl-1,8-naphthalimide.

In one aspect, the disclosure provides a chemical probe comprising 4-ethynyl-N-ethyl-1,8-naphthalimide. In another aspect, the disclosure provides a fluorogenic probe produced by contacting the chemical probe with an azido-derivatized molecule.

In one aspect, the disclosure provides a chemical probe comprising 4-azido-N-ethyl-1,8-naphthalimide. In another aspect, the disclosure provides a fluorogenic probe produced by contacting the chemical probe with an alkynyl-derivatized molecule.

In one aspect, the disclosure provides a method of labeling a glycoconjugate, the method comprising: incubating an alkynyl-derivatized fucose-GDP analog with a glycoconjugate and a fucosyltransferase to create an alkynyl-derivatized glycoconjugate; and contacting the alkynyl-derivatized glycoconjugate with a chemical probe wherein said chemical probe reacts with said alkynyl group in the alkynyl-derivatized glycoconjugate to create a labeled glycoconjugate. In a specific aspect, the chemical probe is 4-azido-N-ethyl-1,8-naphthalimide. In a further aspect, the labeled glycoconjugate is a fluorescently labeled fucosylated glycoconjugate.

BRIEF DESCRIPTION OF THE FIGURES

FIG. 3 shows the "click" reaction of probes 1a and 1b with fucose derivatives (A) and fluorescence spectra of compounds 1a and 1b and their click products 3a and 3b (B and C).

FIG. 5 shows analysis of fucosylated glycoconjugates on the cell surface of Jurkat cells by flow cytometry.

FIG. 6 shows fluorescent image of cells labeled with probe 1a.

DETAILED DESCRIPTION

Figure 1:
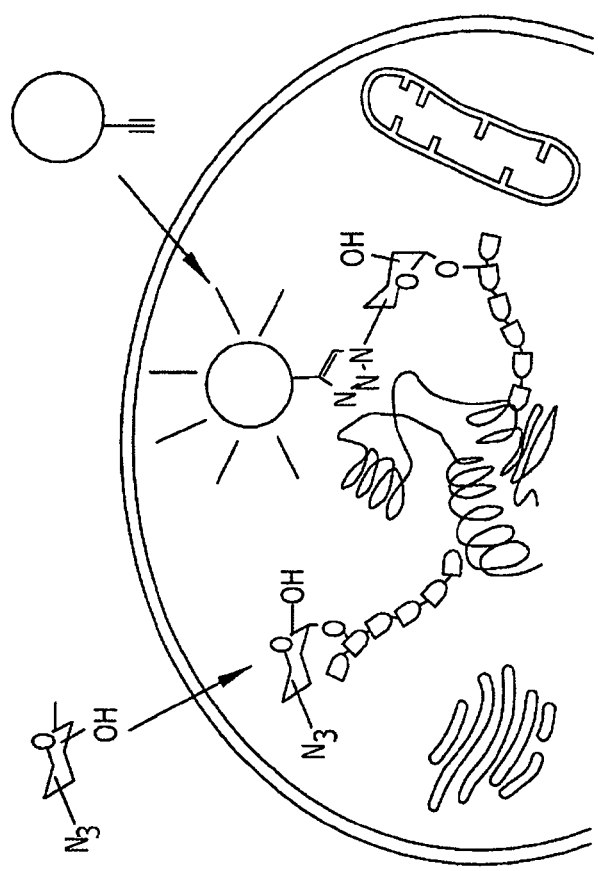
FIG. 1 shows the general strategy for glycan labeling: (A) probe structures (B) strategy for specific fluorescent labeling of fucosylated glycans in cells.
Figure 1:
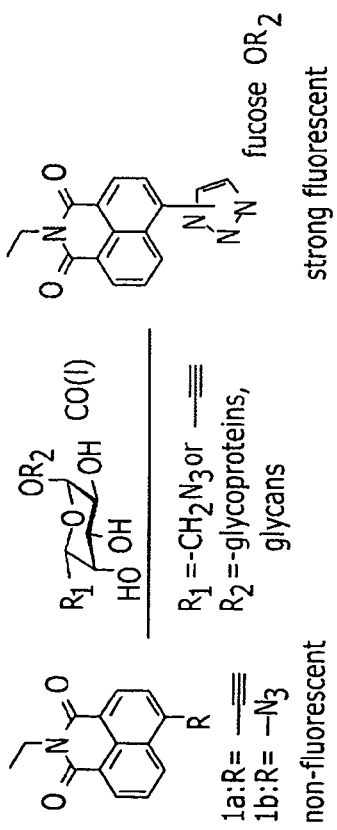

As used herein, the term "alkynyl group" or "alkyne functional group" means an alkyne functional group (also called acetylene functional group), which is a hydrocarbon comprised of a triple bond between two carbon atoms.

As used herein, the term "alkynyl-derivatized sugar" means a synthetic sugar analog, in pro-molecular, metabolic precursor, and/or downstream metabolite form, substituted with an alkynyl group.

As used herein, the term "alkynyl-tagged", means a glycoconjugate incorporating an alkynyl-derivatized sugar.

As used herein, the terms "alkynyl fucose," "alkynyl Fuc" and "Fucyne" are used interchangeably.

As used herein, the term "alkynyl N-acetylmannosamine," "alkynyl ManNAc" and "ManNAcyne" are used interchangeably.

As used herein, the term "alkynyl sialic acid," "alkynyl NeuAc" and "NeuAcyne" are used interchangeably.

Amino acid residues in peptides shall hereinafter be abbreviated as follows: Phenylalanine is Phe or F; Leucine is Leu or L; Isoleucine is IIe or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W.H. Freeman & Co., New York 1983.

As used herein, the term "Bioorthogonal" means chemical reactants and reactions that are compatible with living systems. Bioorthogonal reactions proceed in high yield under physiological conditions and result in covalent bonds between reactants that are otherwise stable in these settings.

As used herein, the term "Bioorthoganal Chemical Reporting Group" means a non-native, non-perturbing, inert chemical functional group, which can be modified in biological systems by chemo-selective reactions with exogenously delivered probes.

As used herein, the term "cellular glycan" or "cell glycan" refers to a glycan (either alone or as part of a glycoconjugate) that may be at the cell surface, intracellular, or within a cell lysate.

As used herein, the term "Chemoselective" means the preferential reaction of a chemical reagent with only one out of two or more different available functional groups.

As used herein, the term "Coumarin" means any of a group of fluorogenic compounds related to benzopyrone or 2-chromenone that are capable of fluorescence modulation dependent on position of substitution and identity of functional groups.

As used herein, the term "Click-Activated" means any reaction that bioorthogonally proceeds in a manner that changes the chemical and/or physical properties of the resultant molecule.

As used herein, the term "Cycloaddition" means a chemical cyclization reaction, in which two π bonds are lost and two a bonds are gained—the reaction can proceed catalyzed or uncatalyzed or in a concerted or stepwise manner.

As used herein, the term "derivatization" is used to describe a technique used in chemistry which transforms a chemical compound into a product of similar chemical structure, called a derivative. For example, when reference is made to a sugar analog or precursor that has been "derivatized" with an alkyne group, it is meant that the sugar analog is bearing an alkynyl group.

As used herein, the term "Flow cytometry" or "FACS" means a technique for examining the physical and chemical properties of particles or cells suspended in a stream of fluid, through optical and electronic detection devices.

As used herein, the term "Fluorescent Labeled" means derivatizing a molecule with a fluorescent material.

As used herein, the term "Fluorogenic" or "Fluorescent Reporting Group" means a material capable of supporting a chemical reaction dependent on the presence of a particular analyte material. Said analyte-dependent chemical reaction reaction produces a fluorescent reporting molecule.

As used herein, the term "Fluorescent" means a material exhibiting fluorescence.

As used herein, the term "Fucose" (Fuc) means a six-carbon deoxy pyran sugar, distinguished from other hexoses by a L-configuration and an unsubstituted carbon at the 6-position.

As used herein, the term "Fucosyltransferase (FucT)" means an enzyme that transfers a fucose from a donor substrate, GDP-fucose (GDP=Guanosine diphosphate), to an acceptor substrate, a glycoconjugate or glycan.

As used herein, the term "fucosylated" or "fucosyl" means a molecule (typically a glycoconjugate or glycan) that has been covalently appended with a Fuc residue (typically by a FucT)

As used herein, the term "GDP analog" means a molecular derivative of Guanosine diphosphate (GDP).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans are typically comprised of monosaccharides linked together with O-glycosidic bonds. For example, cellulose is a glycan (or more specifically a glucan) composed of beta-1,4-linked D-glucose, and chitin is a glycan composed of beta-1,4-linked N-acetyl-D-glucosamine. Glycans can be homo or heteropolymers of monosaccharide residues, and can be linear or branched. Glycans can be found attached to lipids and proteins, as in glycoproteins and proteoglycans. They are generally found on the exterior surface of cells. O— and N-linked glycans are very common in eukaryotes but may also be found, although less commonly, in prokaryotes. N-linked glycans are attached through amide bonds to asparagine residues found in the N-glycosylation consensus sequon. The sequon is a Asn-X-Ser or Asn-X-Thr sequence, where X is any amino acid except proline. O-linked glycans are attached through glycosidic bonds with oxygen groups on serine and threonine residues in proteins, or hydroxyl groups of lipids and small molecules.

As used herein, the term "Glycoconjugate" means a molecule covalently modified with glycans.

As used herein, the term "Glycoprotein" means a protein covalently modified with glycan(s). There are four types of glycoproteins: 1) N-linked glycoproteins, 2) O-linked glycoproteins (mucins), 3) glucosaminoglycans (GAGs, which are also commonly called proteoglycans), 4) GPI-anchored. Most glycoproteins have structural micro-heterogeneity (multiple different glycan structures attached within the same glycosylation site), and structural macro-heterogeneity (multiple sites and types of glycan attachment).

As used herein, the term "glycoproteomics" refers to a branch of proteomics that identifies, catalogs, and characterizes proteins containing carbohydrates as a post-translational modification. Glycoproteomics also refers to the study of a cell, tissue, or organism's glycan and glycoprotein content at any point in time.

As used herein, the term "Glycosylation" means the enzymatic transfer of saccharides or oligosaccharide chains onto glycoconjugates. Protein glycosylation is a complex co- or post-translational process that modifies the majority of the human proteome, vastly expanding its functional repertoire.

As used herein, the term "isolated" means glycoconjugates that can be selectively separated by secondary detection means.

As used herein, the term "Labeled Glycoprotein" means a glycoprotein covalently attached via cycloaddition to a moiety that can facilitate the manipulation of the "labeled glycoprotein," such as the isolation, visualization, detection, and quantification of the labeled glycoprotein.

As used herein, the term "Liquid chromatography-mass spectrometry" or "LC-MS" refers to an analytical chemistry technique that combines the physical separation capabilities of liquid chromatography (aka HPLC) with the mass analysis capabilities of mass spectrometry (MS). LC-MS is a powerful technique used for many applications which has very high sensitivity and specificity. Generally its application is oriented towards the specific detection and potential identification of chemicals in the presence of other chemicals (in a complex mixture). LC-MS is also used in the study of proteomics where components of a complex mixture must be detected and identified in some manner. The bottom-up proteomics LC-MS approach to proteomics generally involves protease digestion (usually Trypsin) followed by LC-MS with peptide mass fingerprinting or LC-MS$^2$ (tandem MS) to derive the sequence of individual peptides.

As used herein, the term "Metabolic Oligosaccharide Engineering" or "MOE" means the process of incorporating an alkynyl-derivatized sugar into a glycoconjugate.

As used herein, the term "MudPIT" or Multidimentional Protein Identification Technology refers to the characterization of protein mixtures using tandem LC-MS$^2$. A peptide mixture that results from digestion of a protein mixture is fractionated by multiple steps of liquid chromatography. The eluent from the chromatography stage can be either directly introduced to the tandem MS through electrospray ionization, or laid down on a series of small spots for later mass analysis using MALDI.

As used herein, the term "proteome" refers to the entire complement of proteins expressed by a genome, cell, tissue or organism. More specifically, it is the expressed proteins at a given time point under defined conditions.

As used herein, the term "proteomics" refers to the study of the proteome. Proteomics has largely been practiced through the separation of proteins by two dimensional gel electrophoresis. In the first dimension, the proteins are separated by isoelectric focusing, which resolves proteins on the basis of charge. In the second dimension, proteins are separated by molecular weight using SDS-PAGE. The gel is dyed with Coomassie Blue or silver stain to visualize the proteins. Spots on the gel are proteins that have migrated to specific locations. The mass spectrometer has augmented proteomics. Peptide mass fingerprinting identifies a protein by cleaving it into short peptides and then deduces the protein's identity by matching the observed peptide masses against a sequence database. Tandem mass spectrometry, on the other hand, can get sequence information from individual peptides by isolating them, colliding them with a non-reactive gas, and then cataloging the fragment ions produced.

As used herein, the term "Reporting Group" means a molecule that has properties capable of providing detectable feedback about events transpiring in a test system (from a controlled in vitro assay to a complex biological system).

As used herein, the term "sialylated" or "sialyl" means a molecule (typically a glycoconjugate or glycan) that has been covalently appended with a sialic acid (NeuAc) residue (typically by a sialyl transferase)

As used herein, the term "tagged" means a glycoconjugate that has incorporated an alkynyl-derivatized sugar through any permissive biosynthetic pathway involved in glycoconjugate synthesis.

Disclosed herein is a rapid, versatile, and specific bioorthogonal-labeling approach for cellular glycans that are first metabolically tagged with azide groups and then labeled using the Cu(I)-catalyzed azide-alkyne [3+2]cycloaddition reaction, CuAAC or click chemistry. The disclosed method entails generating a fluorescent glycan probe from a nonfluorescent precursor, 4-ethynyl-N-ethyl-1,8-naphthalimide, by clicking the fluorescent trigger, the alkyne at the 4 position, via CuAAC with an azido-modified sugar.

FIG. 1 shows the general strategy for glycan labeling. In FIG. 1(A) probe structures based on 1,8-naphthalimide include an azide or alkyne at a position of the ring that will allow a fluorogenic ligation with 6-modified fucose analogs. The fluorescent adduct is generated when probes are reacted with the azido/alkynyl group of fucosides via CuAAC. In FIG. 1(B), a strategy for specific fluorescent labeling of fucosylated glycans in cells is shown. Covalent modification of the target glycan with probes 1a or 1b results in production of fluorescently labeled glycoproteins that had been tagged with modified fucose (azidofucose shown). In each case, any unreacted probe remains traceless, or non-fluorescent.

Figure 2:
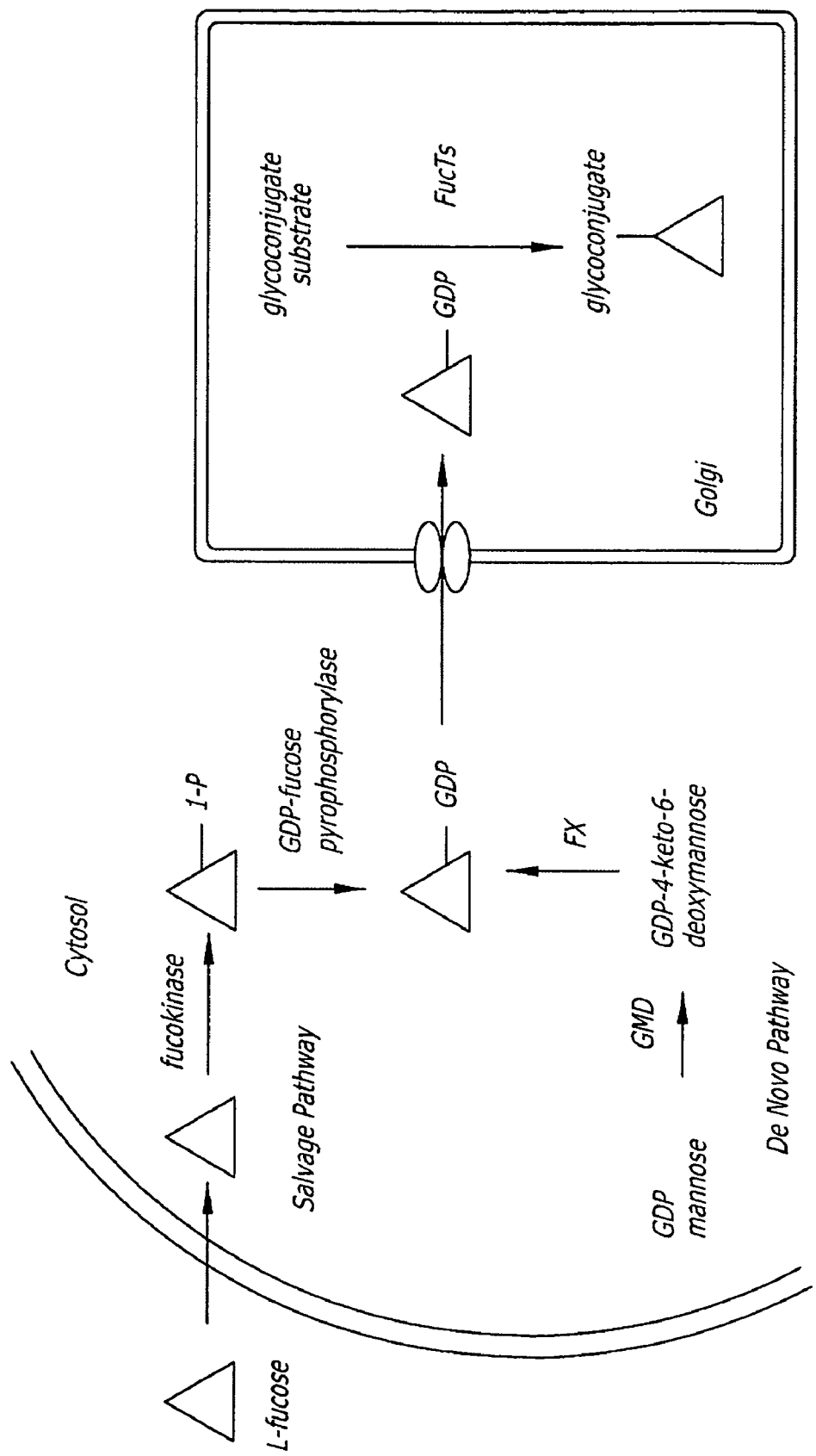
FIG. 2 shows biosynthetic pathways for GDP-fucose.

The incorporation of exogenous natural or unnatural sugars into glycans is achieved by cellular biosynthetic pathways. These processes involve multistep enzymatic transformations that render free sugars in the cytosol into nucleotide-donor sugars, the substrates for glycosyltransferases. Two pathways, the de novo pathway and the salvage pathway, have been proposed in the synthesis of the fucose donor, GDP-fucose, which is used in the construction of fucosylated oligosaccharides (FIG. 2). Modifications at the 6-position of Fuc are tolerated by the salvage pathway and fucosyltransferases.

It is herein disclosed that azido and/or alkyne-modified fucose analogs can be incorporated into glycoproteins via the salvage pathway, since the small size and bioorthogonality of azido/alkynyl groups is herein shown to be tolerated by the requisite enzymes.

FIG. 2 shows biosynthetic pathways for GDP-fucose. The de novo pathway transforms GDP-mannose into GDP-fucose via two enzymes, GDP-mannose 4,6-dehydratase (GM D) and GDP-keto-6-deoxymannose 3,5-epimerase/4-reductase (FX protein). The salvage pathway utilizes free fucose in the cytosol to create GDP-fucose by the action of fucose kinase and GDP-fucose pyrophosphorylase, which act on fucose derived from extracellular and lysosomal sources. GDP-fucose is used by fucosyltransferases (FucTs) in the Golgi apparatus to catalyze fucose transfer onto glycoconjugates.

One aspect of the present disclosure provides a click-activated fluoregenic probe that is useful for labeling chemically tagged fucose glycans. This probe is especially practical in biological systems because a fluorescent signal is activated only after a highly selective, bioorthogonal ligation event. The probe design utilizes a bioorthogonal-labeling approach based on Cu(I)-catalyzed azide-alkyne [3+2] cycloaddition reaction. Desirable features of this reaction include small, stable coupling partners (the azide and alkyne), fast reaction rates, and the formation of a triazole unit that can trigger the fluorescent emission of click-activated fluorogenic probe via electron-donating properties. In one aspect, this click-activated fluorogenic approach is used to control the fluorescence of coumarins by other groups. However, the coumarin system suffers from UV excitation and short wavelength fluorescence, which might increase the background signal in biological systems. In another aspect, the fluorogenic probe design is based on 4-amino-1,8-naphthalimide, which absorbs light in the visible region and emits at long wavelengths ($\lambda_{max}$ 540-550 nm). The fluorescent signal of 1,8-naphthalimides can be modulated by the formation of a triazole ring, because substitutions at the 4 position with an electron-donating group are known to strongly affect their fluorescent properties. Two 1,8-naphthalimide derivatives are disclosed for click-activated fluorgenic properties (1a and 1b)

with either an azide or alkyne moiety attached at the 4 position. This design provides an opportunity to react the probe with a fucose analog equipped with the corresponding azido or alkynyl functionality using CuAAC. The substrate tolerance of enzymes in the biosynthesis of fucosylated glycoconjugates is used to determine which modified fucose should be implemented.

Using flow cytometry, it is demonstrated that the click-activated fluorogenic naphthalimide probe 1a selectively and fluorescently labels fucosylated glycans on the cell surface after CuAAC with azide-tagged fucose. The modified 6-azidofucose is fed to the cell in acetylated form facilitating incorporation into glycoconjugates through the biosynthetic salvage pathway. A stepwise staining experiment, first using biotinylated alkyne reagent 13 to label tagged glycans with CuAAC and then an avidin-fluorescein conjugate to visualize labeled glycans, confirmed that the CuAAC reaction occurred with tagged glycans on the cell surface. A significant reduction in the fluorescent signal was observed when cells were treated with azidofucose analog and tunicamycin, indicating that most azidofucose tags are presented in the context of N-linked glycoproteins in Jurkat cells. This result is consistent with reports that cell surface glycans displayed on Jurkat cells are primarily N-linked glycoproteins. Click-activated probe 1a also allows for the intracellular imaging of fucosylated glycoconjugates, which can help define their cellular localization. Fluorescent patterns from labeled glycans (labeled with click-activated probe 1a) are observed by fluorescence microscopy, and glycan-labeling co-localizes with a Golgi marker. When azide-tagged cellular glycans are treated with a water-soluble triphenylphosphine before CuAAC with probe 1a, a signal does not develop, indicating that the fluorogenic reaction proceeds specifically and selectively with glycans tagged with azides.

Synthesis of Fluorogenic Probes

Compounds 1a and 1b were synthesized from 4-bromo-1, 8-naphthalic anhydride. Their coupling partners, fucose analogs 2a and 2b, were prepared from L-galactose. Conversion from the 6-hydroxyl group into the alkyne was achieved by using the Seyferth/Gilbert reagent in excellent yield.

Reactivity and click-activated fluorogenic properties of compounds 1a and 1b were tested by performing a Cu(I)-catalyzed azide-alkyne [3+2] cycloaddition (CuAAC) with model fucose analogs 2a and 2b, respectively, as shown in FIG. 3. FIG. 3 shows the CuAAC reaction of probes 1a and 1b with fucose derivatives results in highly fluorescent adducts (A) and fluorescence spectra of compounds 1a and 1b and their click products 3a and 3b (B and C). As expected, the ligation reactions produced in a significant increase in fluorescence intensity. The emission maximum of 3a was 462 nm with a quantum yield of 0.36 when excited at 357 nm. Compound 3b also showed strong emission with a maximum at 422 nm and a quantum yield of 0.29, whereas the parent compound 1b showed no fluorescence. Unfortunately, the reaction rate between alkyne probe 1a and azidofucose 2a was very slow. Although the reaction of azido probe 1b was completed in <30 min. only 10% of 1a was converted to 3a after 24 h by using the same conditions (monitored by LC-MS). The relatively low reactivity of 1a compared with 1b might be explained by the highly reactive aromatic azide on the latter. However, in the presence of the Tris(triazolyl) amine ligand, which is an effective Cu(I) catalyst, the reaction between 1a and 2a was completed within 30 min.

Figure 9:
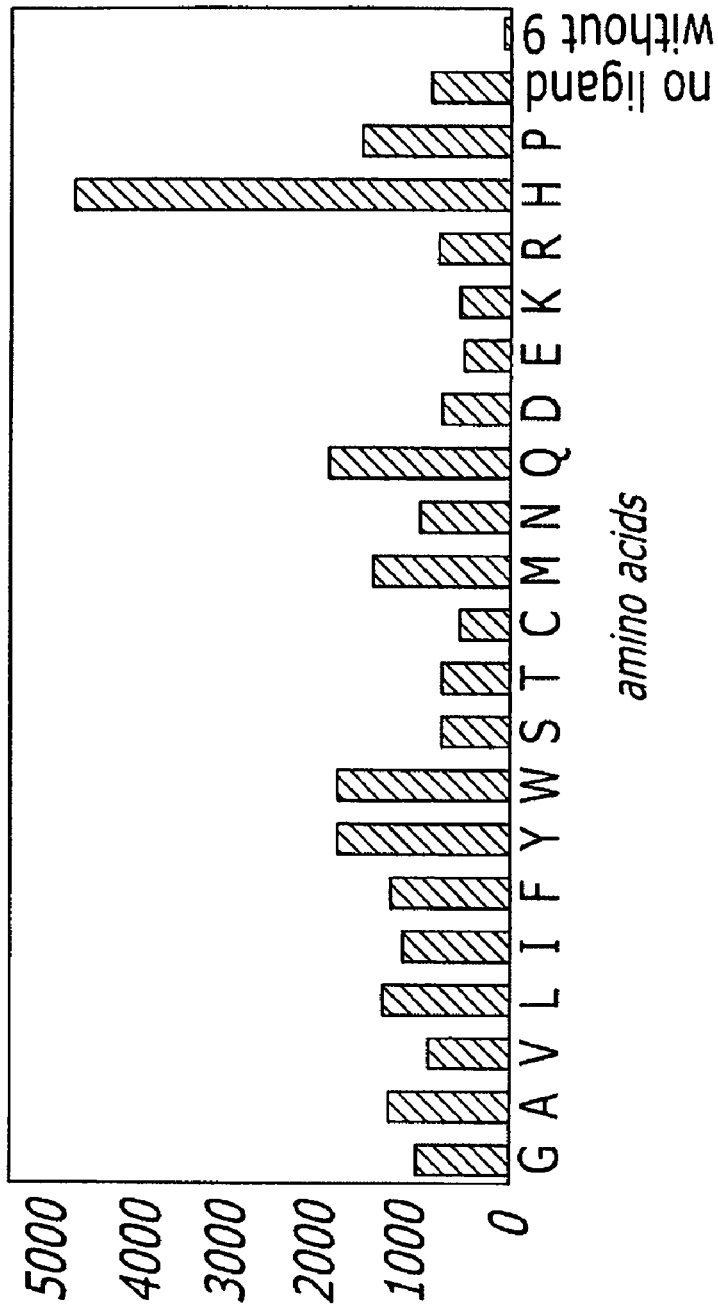
FIG. 9 shows screening of L-amino acids as ligands.

A fluorescence quenching technique was used to identify catalysts for the copper-catalyzed cycloaddition. However, this method has limitations because of a high false-positive rate caused by ligand itself or other side reactions. The slow reaction between 1a and 2a, however, is useful for catalyst screening because of its inherently low background signal. In such a screen, the reaction between 1a and 2a is performed in microtiter plates in the presence of individual amino acids. FIG. 9 shows screening of L-amino acids as ligands. (Upper) The microtiter plate was visualized under long wavelength UV lamp (365 nm). (Lower) The fluorescent intensities of each well are measured by a fluorescence plate reader.

The effect of the ligand effect on the reaction rate was visualized by holding the 96-well microtiter plate under a long wavelength UV lamp (365 nm) and analyzed with a standard fluorescence multiplate reader. The assay identified histidine as the best amino acid ligand catalyst for the Cu(I)-catalyzed 1,3-dipolar cycloaddition reaction. This experiment demonstrates that compound 1a is generally useful for rapid screening of novel catalysts for azide-alkyne cycloaddition reaction.

Fluorescent Labeling of Fucosylated Glycoconjugate

In one aspect, the naphthalimide probes are used to specifically label fucosylated glycoconjugates in vitro. In this aspect, GDP-fucose derivatives 8 and 9, which contain either an acetylene or azido group at the 6 position of the fucose, are synthesized as shown in Scheme 1.

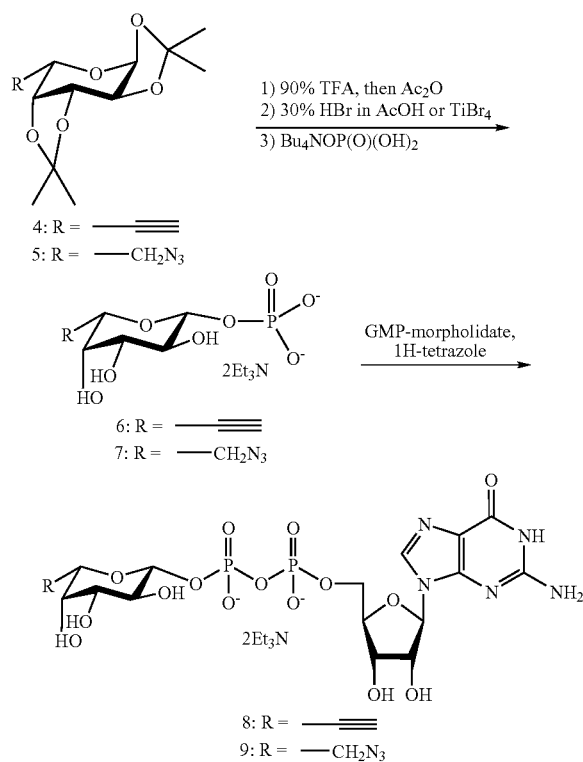

Figure 4:
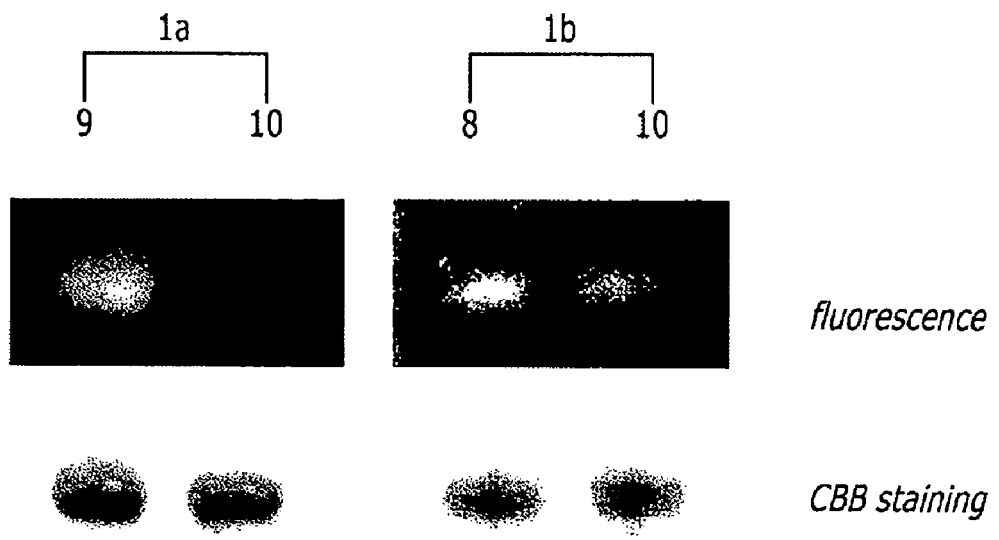
FIG. 4 shows visualization of AGP after FucT transfer of modified GDP-fucose and labeling reaction with fluorogenic probes 1a and 1b.
Figure 4:
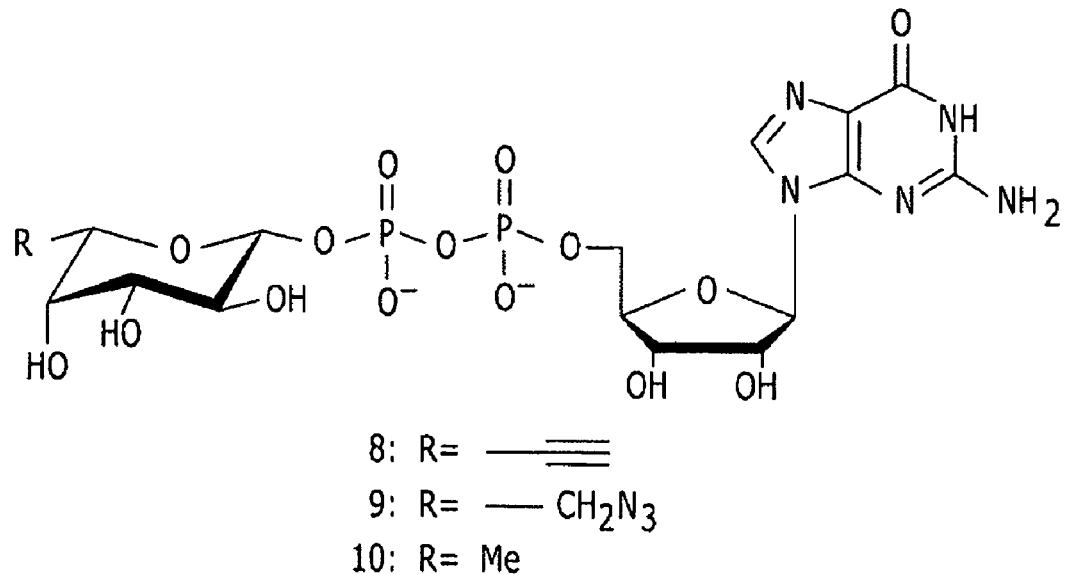

Briefly, fucose analogs 4 and 5 are converted to the corresponding 1-bromides, which then are substituted directly by a phosphate group. Notably, under standard bromination conditions, such as HBr/AcOH and bromotrimethylsilane, the azide is substituted with bromide. Therefore, TiBr₄ is used instead, as described by Srivastava. The fucose-1-phosphates are converted to the corresponding GDP-fucose analogs by using 1H-tetrazole as a catalyst. The tolerability of GDP-fucose analogs 8 and 9 for human alpha-1,3-fucosyl-transeferases (FucTs) II-VII is confirmed by using a standard microtiter plate assay. They are then used to elaborate the glycoconjugate substrate, human alpha$_1$-acid glycoprotein (AGP), an acute-phase protein. As fucosylation of AGP is associated with inflammatory diseases, the degree of fucosylation of AGP could be a potential diagnostic or prognostic marker. AGP was fucosylated by using FucT V in the presence of GDP-fucose analogs 8 or 9. After gel filtration, the fucosylated AGP is labeled by using the corresponding naphthalimide 1a or 1b for 4 h at room temperature. Labeled protein is analyzed by SDS/PAGE and visualized by UV light (365 nm). Both click-activated probes 1a and 1b showed clear fluorescent bands when AGP was fucosylated with analogs 9 and 8, respectively. No band was present when unmodified GDP-fucose 10 was used, indicating a specific ligation between probe 1a and the azidofucose analog transferred onto the protein glycan as shown in FIG. 4. FIG. 4 shows visualization of AGP after FucT transfer of modified GDP-fucose and labeling reaction with fluorogenic probes 1a and 1b. Treated protein was separated by SDS/PAGE and visualized by UV light (Top) and Coomassie blue staining (CBB) (Middle). (Bottom) Modified GDP-fucose. However, the azido probe 1b slowly decomposed into a strongly fluorescent 4-amino derivative, resulting in a slight background signal Thus, the alkyne probe is more reliable for labeling.

Fluorescent Labeling of Fucosylated Glycoconjugates on the Cell Surface

In another aspect, the disclosure provides a method of labeling of azide-tagged glycoconjugates expressed on the cell surface by using the alkyne click-activated fluorogenic probe 1a. First, the effect of various Cu(I) sources on the copper-catalyzed cell-surface labeling reaction was investigated. Cu(I) is typically generated including in situ by the reduction of Cu(II) by conventional reducing agents or the direct addition of Cu(I) as a salt. To label azido tagged glycoconjugates (in this case, cellular glycans that had incorporated azidofucose), we investigated both methods by using in situ Cu(II) reduction with ascorbic acid and Tris(carboxyethyl)phosphine (TCEP) and direct addition of Cu(I), via CuBr, in CuAAC reactions. Jurkat cells were cultured in the presence of globally acetylated 6-azido-L-fucose 12 (acetylation increases cellular uptake of the sugar) so that they will incorporate the analog via the salvage pathway. After incubating for 3 days, the cells were labeled with 1a in the presence of the above listed Cu(I) sources, and the fluorescent intensities were measured by flow cytometry. The azidofucose-treated cells exhibited a distinct increase in fluorescence by using all three copper sources, when compared with cells treated with natural fucose as shown in FIG. 5A. FIG. 5 shows analysis of azide bearing fucosylated glycoconjugates that have been CuAAC-labeled with 1a on the cell surface of Jurkat cells by flow cytometry. FIG. 5A shows the comparison of the labeling efficiency of the various copper sources including CuSO₄/ascorbic acid, CuSO₄/TCEP, or CuBr. Data points represent the average of triplicate experiments. FIG. 5B shows that co-treatment with azdiofucose and tunicamycin, an inhibitor of N-glycosylation, suppressed cell surface fluorescence (cells cultured with fucose in red, azidofucose in green, or azidofucose in the presence of tunicamycin in black). This result indicates that most of the azidofucose was incorporated into N-linked glycoproteins and excludes the possibility that the fluorescence was generated by any remaining free azidofucose. FIG. 5C shows azide-tagged glycoconjugates CuAAC-labeled with biotinylated alkyne 13, detected with UltraAvidin-Fluorescein, and then analyzed by flow cytometry (cells treated with fucose in red or azidofucose in green). This result demonstrates that fluorescence results from the specific fluorogenic modification of azido-glycans. The CuBr-mediated CuAAC azido glycan labeling produced the highest mean fluorescent intensity (MFI) by flow cytometry, in agreement with previous literature.

In another aspect, the azido-tagged glycoconjugates are displayed on the cell surface, as shown by stepwise staining with a biotinylated alkyne reagent 13. The azidofucose-treated cells are labeled with biotinylated alkyne 13 and then stained with an avidin-fluorescein conjugate that is not taken up by the cells. There is a distinct increase in fluorescent signal when the cells are treated with azidofucose 12 versus fucose as shown in FIG. 5C suggesting azido-tagged fucose glycans are presented on the cell surface where the azide reactive group can be used for selective labeling with azide-alkyne cycloaddition reactions. These results demonstrate that the azidofucose-treated cells express azido-fucosylated glycoconjugates on the cell surface. Moreover, they can be specifically and selectively visualized by labeling them with an alkyne probe using Cu(I)-catalyzed [3+2] cycloaddition.

Visualization of Fucosylated Glycoconjugates Inside the Cell

Figure 6:
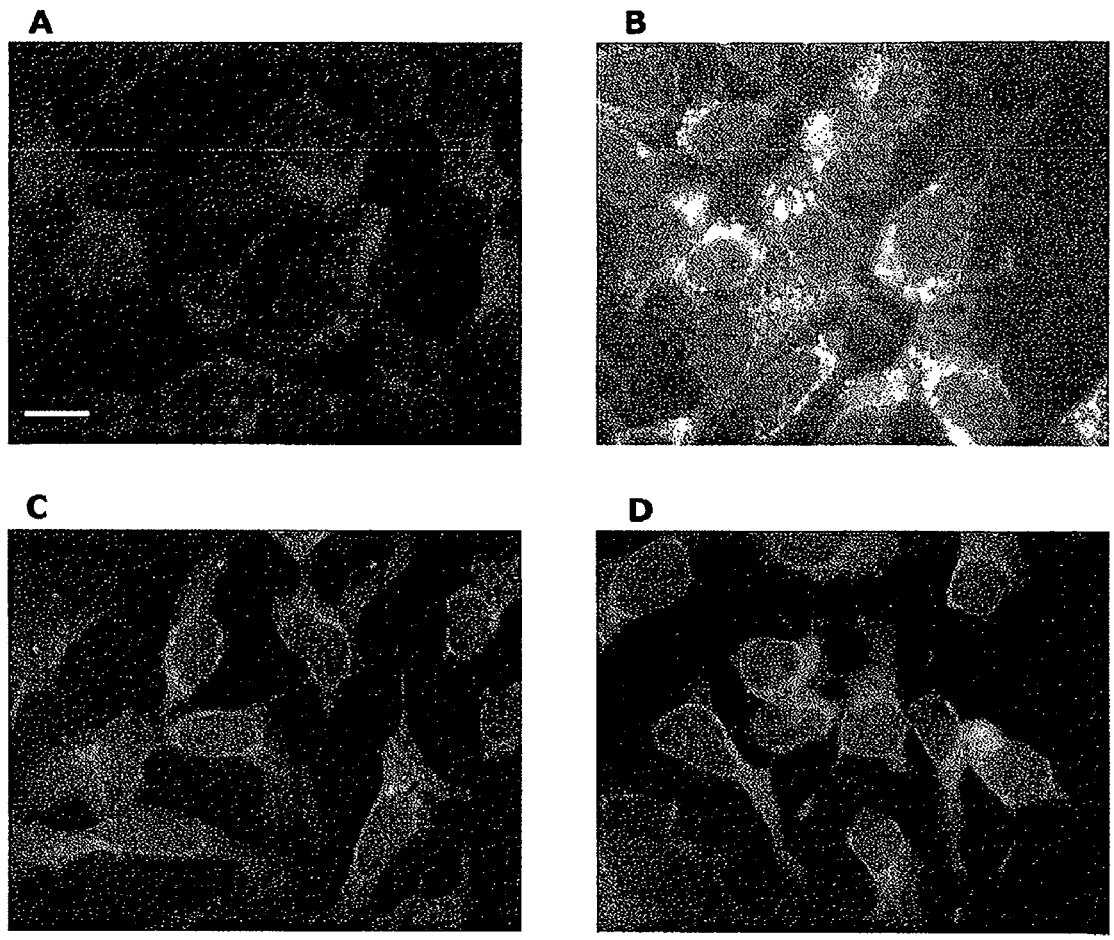

In one aspect, the disclosure provides a method of using the naphthalimide probe for intracellular imaging, as demonstrated by fluorescence microscopy. The human hepatoma cell line, Hep 3B, was incubated with acetylated azidofucose 12. After 3 days, the cells were fixed, washed with PBS, and then stained with 1a for visualization. Compared with the cells incubated with control fucose as shown in FIG. 6A, a distinct punctate-labeling pattern was observed in cells incubated with azidofucose 12 as shown in FIG. 6B. FIG. 6 shows fluorescent image of cells labeled with probe 1a. The labeling reaction was performed in the presence of Cu(I) after the treatment with control fucose (A) or azidofucose 12 (B), or in the absence of Cu(I) after the treatment with control fucose (C) or azidofucose 12 (D). (Scale bar: 20 μm.)

Figure 7:
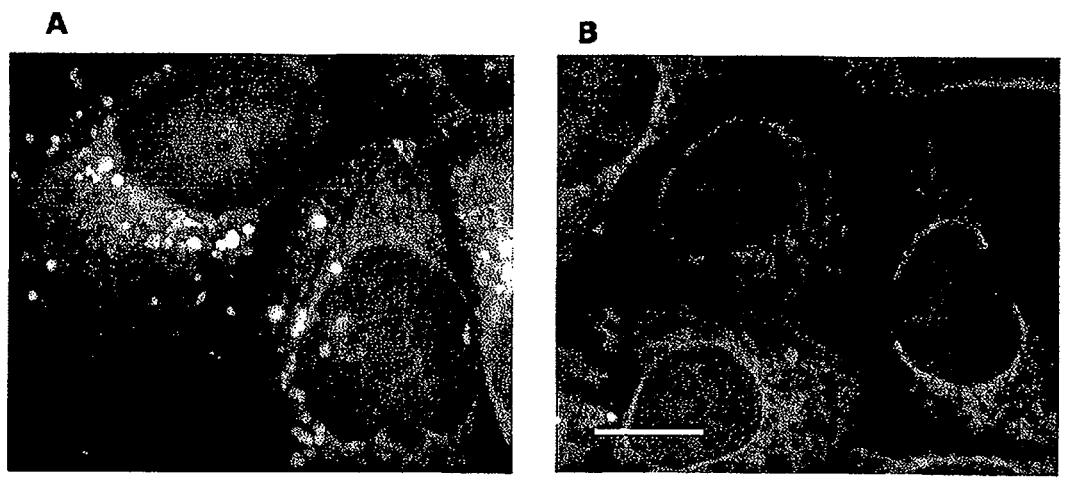
FIG. 7 shows specificity of the Cu(I)-catalyzed cycloaddition for azidofucose.

To confirm that the imaging data were α-specific click-activated phenomenon between the azide tagged glycans and probe 1a, cells with azide-tagged glycans were treated with a water-soluble trisulfonated triphenylphosphine, which will selectively reduce azide groups. After reduction, the cells subjected to CuAAC with 1a showed minimal fluorescence by microscopy, as in the case of fucose control cells shown in FIG. 7. FIG. 7 shows specificity of the Cu(I)-catalyzed cycloaddition for azidofucose residues that have been incorporated into cellular glycans. Azidofucose-supplemented cells were fixed and labeled with probe 1a under CuAAC (A) or were reduced with Tris(3-sulfonatophenyl)phosphine and then subjected to the same labeling conditions (B). (Scale bar: 20 μm.)

The click-activated fluorogenic probe labeling provides sufficient a signal-to-noise ratio to allow direct analysis of azidofucosylation intracellularly.

Figure 8:
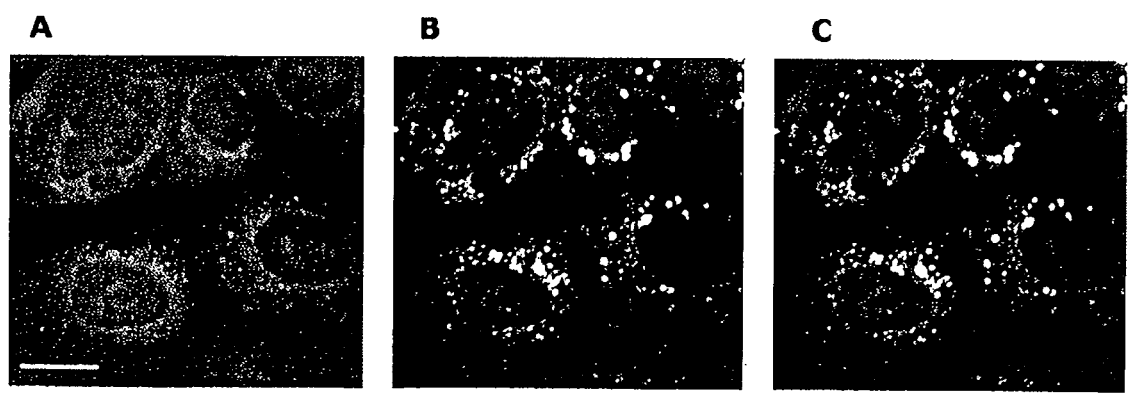
FIG. 8 shows imaging intracellular fucosylation by double staining with the probe 1a and WGA lectin.

In another aspect of the disclosure, double-staining experiments were performed to find out whether the punctate pattern observed from azidofucose marks specific cellular compartments. FIG. 8 shows intracellular imaging by double staining, with azido fucosylation marked by CuAAC labeling with probe 1a (blue), and the Golgi organelle marked by WGA lectin (red). Azidofucose treated cells were fixed and labeled with probe 1a and then further treated with WGA lectin conjugated with Alexa Fluor 594, and the cells were imaged with confocal fluorescence microscope, using the appropriate filter sets. FIG. 8A shows blue fluorescence, resulting from probe 1a conjugated to azidofucose groups. FIG. 8B shows red fluorescence, stained with Alexa Fluor 594-conjugated WGA lectin as a Golgi marker. FIG. 8C shows purple color, overlap in blue and red signals. (Scale bar: 20 μm.)

As shown in FIG. 8, azidofucose labeling overlapped perfectly with Alexa Fluor 594-conjugated wheat germ agglutinin (WGA) lectin staining. The WGA lectin binds to sialic acid and N-acetylglucosaminyl residues of glycoproteins and is commonly used as a Golgi marker. These data further document the specific nature and sensitivity of the click-activated fluorogenic probe, allowing visualization of fucosylated glycoproteins intracellularly.

The disclosed click-activated fluorogenic-labeling technique permits imaging of tagged fucosylated glycoconjugates at the cell surface and inside the cell. Because of the high structural complexity of carbohydrates and the diversity of glycans, many functions of fucosylated glycoconjugates remain to be elucidated. Fluorescent labeling represents a way to address some of the questions concerning the structure, function, and trafficking of fucosylated glycans. The herein disclosed methods also facilitate a comparison of fucosylation in normal and tumor cells. The disclosed methods also allow monitoring of particular fucosylated glycoconjugates after inhibition of specific FucTs with small molecules or RNAi.

EXAMPLES

Example 1

Analysis of Fluorescent Labeling at the Cell Surface by Flow Cytometry

Jurkat cells were cultured in RPMI medium 1640 (Invitrogen, Carlsbad, Calif.), supplemented with 10% FCS and peracetylated fucose 11 or azidofucose 12 (200 μM) at a density of $2 \times 10^5$ cells per ml for 3 days, in the presence or absence of tunicamycin (5 μg/ml). After washing with 0.1% FCS/PBS, $10^6$ cells were resuspended in 100 μl of a reaction solution (0.1 mM probe 1a or biotinylated alkyne 13/0.2 mM Tris-triazoleamine catalyst/0.1 mM CuBr in PBS) at room temperature for 30 min, followed by washing with 0.1% FCS/PBS. For the biotinylation experiment, cells were stained with 0.25 μg of UltraAvidin-Fluorescein (Leinco Technologies, St. Louis, Mo.) in 50 ml of staining buffer (1% FCS/0.1% $NaN_3$ in PBS) for 30 min at 4° C., followed by three washes with staining buffer. The fluorescence intensity was detected and acquired by BD LSR II (BD Biosciences, San Jose, Calif.) and FACSDiva software (BD Biosciences). Twenty thousand events were collected in each sample. Data analysis was performed with CellQuest Pro software (BD Biosciences). For detection of the fluorescent adduct with probe 1a, a 351-nm UV laser was used for excitation, and emission was detected by a 440/40 band-pass filter.

Example 2

Fluorescence Microscopy and Imaging

The human hepatocellular carcinoma cell line, Hep3B (American Type Culture Collection, Manassas, Va.), was cultured in Opti-MEM (Invitrogen) supplemented with 0.1% FCS and treated with natural fucose or peracetylated azidofucose 12 (200 μM) for 3 days. The cells then were transferred to a coverslip glass slide and cultured overnight in the same medium. The cells were fixed by acetone and labeled as follows. Fixed cells were incubated with 0.2 mM probe 1a/2.0 mM Tris-triazoleamine catalyst/1.0 mM $CuSO_4$/2.0 mM sodium ascorbate in PBS at room temperature overnight. After labeling, cells were washed with PBS, and fluorescence images were obtained by using Axiovert 200M (Carl Zeiss, Inc., Thornwood, N.Y.). For counter staining of Golgi compartments, the fixed cells were stained by using Alexa Fluor 594 conjugated WGA lectin (Invitrogen), and each fluorescent dye was imaged by using Bio-Rad (Carl Zeiss) Radiance 2100 Rainbow laser scanning confocal microscopy system.

Chemical Synthesis

All chemicals were purchased as reagent grade and used without further purification. Reactions were monitored with analytical thin-layer chromatography (TLC) on silica gel 60 F254 plates and visualized under UV (254 nm) and/or by staining with 5% sulfuric acid or acidic ceric ammonium molybdate. $^1H$— or $^{13}C$-NMR spectra were measured on a Bruker DRX-500 or DRX-600 using $CDCl_3$ or DMSO-$d_6$ as the solvent ($^1H$, 500 or 600 MHz; $^{13}C$, 125 or 150 MHz). Chemical shifts (in ppm) were determined relative to either tetramethylsilane (0 ppm) or deuterated chloroform (77 ppm). Mass spectra were obtained by the analytical services of this Department. Fluorescent excitation and emission were recorded using a HITACHI F-2000 fluorescence spectrophotometer. Quantum yields were determined using Quinine sulfate as the fluorescent standard (0.54). LC-MS analysis was carried out on a Agilent 1100 Series LC/MSD. Human alpha$_1$-acid glycoprotein and alpha-fucosidase were purchased from Sigma and human alpha-1,3-fucosyltransferase V was from CalBiochem.

Example 3

4-Ethynyl-N-ethyl-1,8-naphthalimide (1a)

As shown in Scheme 2, to a solution of 4-bromo-N-ethyl-1,8-naphthalimide 15 (234 mg, 0.77 mmol) in 10 mL of THF was added tetrakis(triphenylphosphine)palladium (90 mg, 0.078 mmol), CuI (30 mg, 0.16 mmol), trimethylsilylacetylene (0.54 mL, 3.82 mmol) and N,N-diisopropylethylamine (0.5 mL, 2.87 mol) under argon gas. The mixture was stirred at room temperature overnight. The reaction mixture was diluted with AcOEt, and washed with saturated $NH_4Cl$ solution, dried over $Na_2SO_4$, and evaporated. The residue was purified partially by flash column chromatography on silica gel (AcOEt/hexane 1:10) to give the corresponding trimethylsilyl compound (180 mg). To a solution of this compound (180 mg) in 25 mL of MeOH was added 1M tetrabutylammonium fluoride solution in THF (2 mL, 2 mmol), and the mixture was stirred at 60° C. for 15 min. The reaction mixture was diluted with water, and the precipitates were collected by filtration. The solids were purified by flash column chromatography on silica gel (AcOEt/hexane 1:5) to afford 1a as a colorless solid (65 mg, 34%); $^1H$-NMR (500 MHz, $CDCl_3$) δ 1.34 (t, 3H, J=7.0 Hz), 3.73 (s, 1H), 4.25 (q, 2H, J=7.0 Hz), 7.83 (m, 1H), 7.94 (d, 1H, J=7.5 Hz), 8.54 (d, 1H, J=7.3 Hz); 8.64 (d, 1H, J=7.5 Hz), 8.67 (d, 1H, J=8.5 Hz); ESI-TOF-HRMS m/e calculated for $(M+H)^+C_{16}H_{12}NO_2$ 250.0863; found 250.0866.

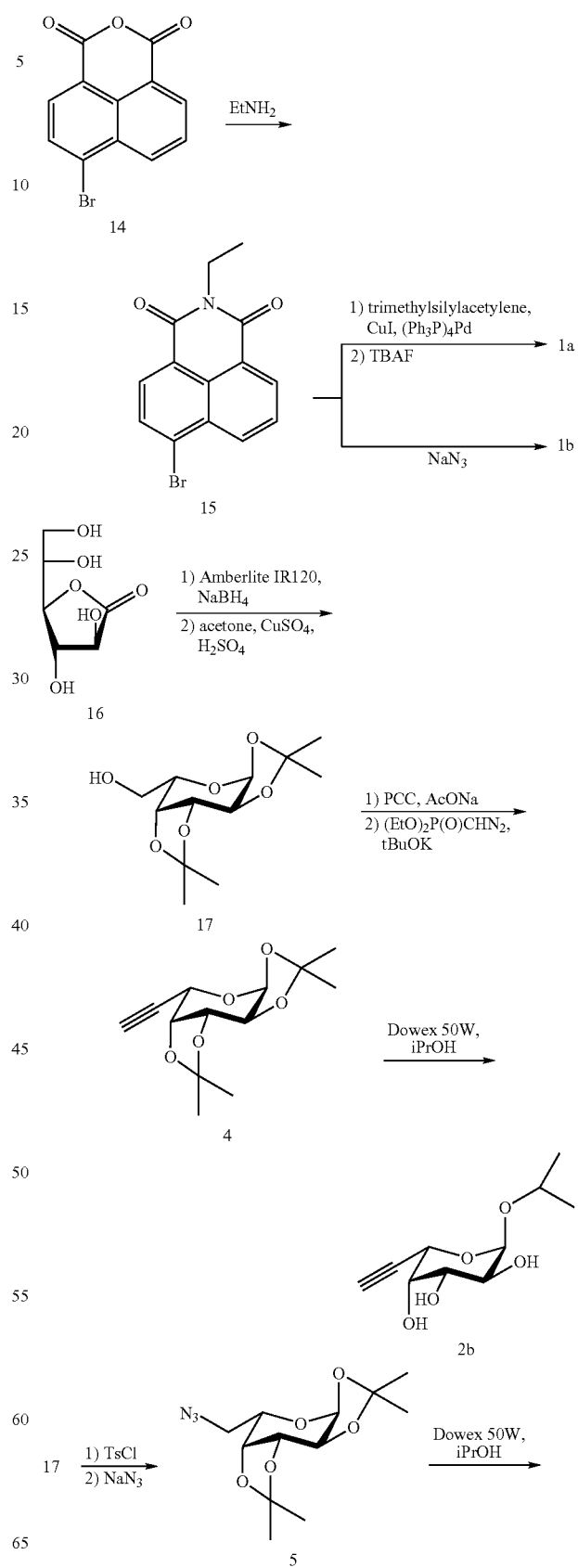

Scheme 2

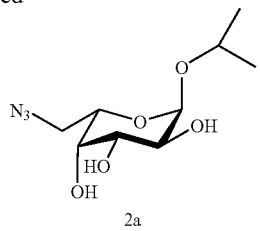

2a

Example 4

4-Azido-N-ethyl-1,8-naphthalimide (2a)

A mixture of 15 (912 mg, 3.0 mmol) and sodium azide (975 mg, 15 mmol) in 12 mL of N-methylpyrrolidinone was stirred at 110° C. for 1 h. The reaction mixture was diluted with water and extracted with AcOEt. The organic layer was washed with brine, dried over $Na_2SO_4$, and evaporated. The residue was purified by flash column chromatography on silica gel (AcOEt/hexane 1:5->1:3) to afford 1b as a yellow solid (540 mg, 68%); $^1$H-NMR (500 MHz, $CDCl_3$) δ 1.33 (t, 3H, J=6.9 Hz), 4.24 (q, 2H, J=6.9 Hz), 7.47 (d, 1H, J=8.3 Hz), 7.75 (m, 1H), 8.44 (d, 1H, J=8.3 Hz), 8.59 (d, 1H, J=7.8 Hz), 8.65 (d, 1H, J=7.3 Hz); ESI-TOF-HRMS m/e calculated for $(M+Na)^+$ $C_{14}H_{11}N_4O_2Na$ 289.0696; found 289.0694.

Example 5

1,2:3,4-Di-O-isopropylidene-alpha-L-galactose (17)

To L-galactono-1,4-lactone (10 g, 56.1 mmol) in MeOH (60 mL) and water (250 mL) at 0° C. was added Amberlite IR 120 ($H^+$) resin (50 mL). $NaBH_4$ (2.2 g, 56.1 mmol) was added portionwise, and the reaction mixture was stirred for 1 h at room temperature. The resin was removed by filtration, and the filtrate was evaporated. The residue was dissolved in acetone (220 mL), $CuSO_4$ (22.2 g, 0.14 mol) and $H_2SO_4$ (1 mL) was added and the solution was stirred at room temperature overnight. The $CuSO_4$ was removed by filtration, and the filtrate was neutralized with $Ca(OH)_2$. After removal of $Ca(OH)_2$ and concentration, the residue was purified by flash column chromatography on silica gel (AcOEt/hexane 1:1) to afford 17 (9.1 g, 62%); The analytical data were in agreement with those published.

Example 6

6,7-Deoxy-1,2:3,4-di-O-isopropylidene-alpha-L-galacto-hept-6-ynopyranoside (4)

A suspension of PCC (1.3 g, 6.0 mmol), NaOAc (1.0 g, 12.0 mmol) and 4 Å molecular sieves (2.7 g) in dry $CH_2Cl_2$ (18 mL) was stirred for 1 h. To this mixture was added a solution of 17 (520 mg, 2.0 mmol) in dry $CH_2Cl_2$ (9 mL) dropwise, and the mixture was stirred at room temperature for 2 h. The reaction mixture was diluted with hexane/ether (1:1, 50 mL), and the solution was filtered through a bed of silica-gel. The filtrate was concentrated to give the crude aldehyde. To a suspension of tBuOK (471 mg, 4.2 mmol) in dry THF (5 mL) was added a solution of $(EtO)_2P(O)CHN_2$ (748 mg, 4.2 mmol) in THF (5 mL) at −78° C. and the mixture was stirred at 5 min under $N_2$ gas. To this solution, a solution of the aldehyde in THF (5 mL) was added, and the mixture was allowed to warm to room temperature and continued to stir overnight. The reaction mixture was quenched with 100 mL of water, and the mixture was extracted with $CH_2Cl_2$. The extracts were washed with brine, dried over with $Na_2SO_4$, and evaporated. The residue was purified by flash column chromatography on silica gel (AcOEt/hexane 1:5) to afford 4 as a colorless oil (295 mg, 62%); The analytical data were in agreement with those published.

Example 7

Isopropyl 6,7-deoxy-alpha-L-galacto-hept-6-ynopyranoside (2b)

To a suspension of 50 mg of Dowex 50WX2-200 ($H^+$ form) in 15 mL of isopropanol was added 4 (150 mg, 0.53 mmol), and the mixture was refluxed overnight. The resin was filtered off, and the filtrate was evaporated. The residue was recrystallized from AcOEt to give 2b as a colorless solid (25 mg, 20%); $^1$H-NMR (500 MHz, $CDCl_3$) δ 1.20 (d, 3H, J=6.0 Hz), 1.26 (d, 3H, J=6.4 Hz), 1.98 (m, 1H), 2.55 (m, 1H), 2.60 (m, 1H), 2.74 (m, 1H), 3.75 (m, 1H), 3.81 (m, 1H), 3.99 (m, 1H), 4.05 (m, 1H), 4.66 (m, 1H), 5.03 (d, 1H, J=3.9 Hz); $^{13}$C-NMR (125 MHz, $CDCl_3$) δ21.61, 23.26, 62.35, 68.85, 70.57, 70.59, 70.98, 71.12, 74.75, 96.96; ESI-TOF-HRMS m/e calculated for $(M+Na)^+C_{10}H_{16}O_5Na$ 239.0890; found 239.0892.

Example 8

Isopropyl 6-azido-alpha-L-fucopyranoside (2a)

To a suspension of 50 mg of Dowex 50WX2-200 ($H^+$ form) in 15 mL of isopropanol was added 6-azide-1,2:3,4-di-O-isopropylidene-alpha-L-fucose 5 (150 mg, 0.53 mmol), which prepared from 17 and the mixture was refluxed overnight. The resin was filtered off, and the filtrate was evaporated. The residue was recrystallized from AcOEt-hexane to give 2a as a colorless solid (68 mg, 52%); $^1$H-NMR (500 MHz, $CDCl_3$) δ1.20 (d, 3H, J=6.0 Hz), 1.27 (d, 3H, J=6.4 Hz), 2.29 (br, 3H), 3.34 (dd, 1H, J=4.7 and 12.9 Hz), 3.64 (dd, 1H, 8.1 and 12.9 Hz), 3.77 (m, 2H), 3.93 (m, 1H), 3.99 (m, 2H), 5.03 (d, 1H, J=3.0 Hz); $^{13}$C-NMR (125 MHz, $CDCl_3$) δ 21.69, 23.19, 51.37, 69.27, 69.33, 69.48, 70.84, 71.19, 96.61; ESI-TOF-HRMS m/e calculated for $(M+Na)^+C_9H_{17}N_3O_5Na$ 270.1060; found 270.1062.

Example 9

Typical Experimental Procedure of Cycloaddition Reaction

The overall volume in each vial was 250 microliters containing a solution of 1,8-naphthalimide fluorophore (0.5 mM), the corresponding fucose analog (1.0 mM), $CuSO_4$ (1.0 mM), and sodium ascorbate (5.0 mM) in DMSO/water (56% DMSO). The reactions were allowed to stand at room temperature for 24 hours. The reactions were monitored by LC-MS, which showed that the corresponding products were only produced in each reaction. Preparative scale reaction was performed in a similar manner, and the reaction mixture was purified by flash column chromatography on silica gel.

3a: $^1$H-NMR (600 MHz, $CDCl_3$) δ 0.94 (d, 3H, J=6.1 Hz), 1.08 (d, 3H, J=6.1 Hz), 1.36 (t, 3H, J=7.0 Hz), 3.63 (m, 1H), 3.83 (m, 2H), 4.07 (s, 1H), 4.27 (q, 2H, J=7.0 Hz), 4.38 (m, 1H), 4.76 (m, 1H), 4.83 (m, 1H), 5.00 (m, 1H), 7.80 (m, 1H), 7.93 (d, 1H, J=7.4 Hz), 8.09 (s, 1H), 8.65 (d, 1H, J=7.9 Hz), 8.67 (d, 1H, J=7.0 Hz), 8.97 (d, 1H, J=7.0 Hz); ESI-TOF-HRMS m/e calculated for $(M+H)^+C_{25}H_{28}N_4O_7$ 497.2031; found 497.2022.

3b: $^1$H-NMR (500 MHz, CDCl$_3$) δ 1.25 (d, 3H, J=6.0 Hz), 1.34 (d, 3H, J=6.4 Hz), 1.37 (t, 3H, J=6.9 Hz), 2.05 (br, 1H), 2.85 (br, 1H), 3.03 (br, 1H), 3.96 (m, 1H), 4.02 (m, 1H), 4.05 (m, 1H), 4.28 (q, 2H, J=6.9 Hz), 4.45 (m, 1H), 5.16 (d, 1H, J=3.7 Hz), 5.35 (s, 1H), 7.81 (m, 1H), 7.85 (d, 1H, J=7.8 Hz), 8.23 (s, 1H), 8.26 (d, 1H, J=8.3 Hz), 8.69 (d, 1H, J=7.8 Hz), 8.70 (d, 1H, J=6.9 Hz); ESI-TOF-HRMS m/e calculated for $(M+Na)^+C_{24}H_{26}N_4O_7Na$ 505.1694; found 505.1674.

Example 10

Rapid Screening of Cycloaddition Catalysts using Fluorogenic Probe

The overall volume in each vial was 250 microliters containing a solution of 1,8-naphthalimide 1a (0.5 mM), azidofucose 2a (1.0 mM), CuSO$_4$ (1.0 mM), L-amino acid (1.0 mM) and sodium ascorbate (5.0 mM) in DMSO/water (56% DMSO). The reactions were allowed to stand at room temperature for 24 hours. The reaction mixture was diluted 60 times with 50 mM HEPES buffer (pH 7.2) and then transferred to 96-well microtiter plate, and fluorescence intensity (excitation, 365 nm; emission, 46.0 nm) was determined with a Fusion plate reader (Perkin Elmer/Packard). The assay identified histidine, which is very good metal chelator, as an excellent catalyst for the Cu(I)-catalyzed 1,3-dipolar cycloaddition reaction. Histidine enhanced the reaction rate about 6-times compared to ligand-free conditions. Among the other amino acids, glutamine, tyrosine and tryptophan were found to give approximately 2-fold enhancement of cycloaddition rates. Interestingly, cysteine, glutamic acid, and lysine, which are also known as good metal chelators, were found to be obstructive to the reaction.

Example 11

Stoichiometric Study of L-Histidine

Figure 10:
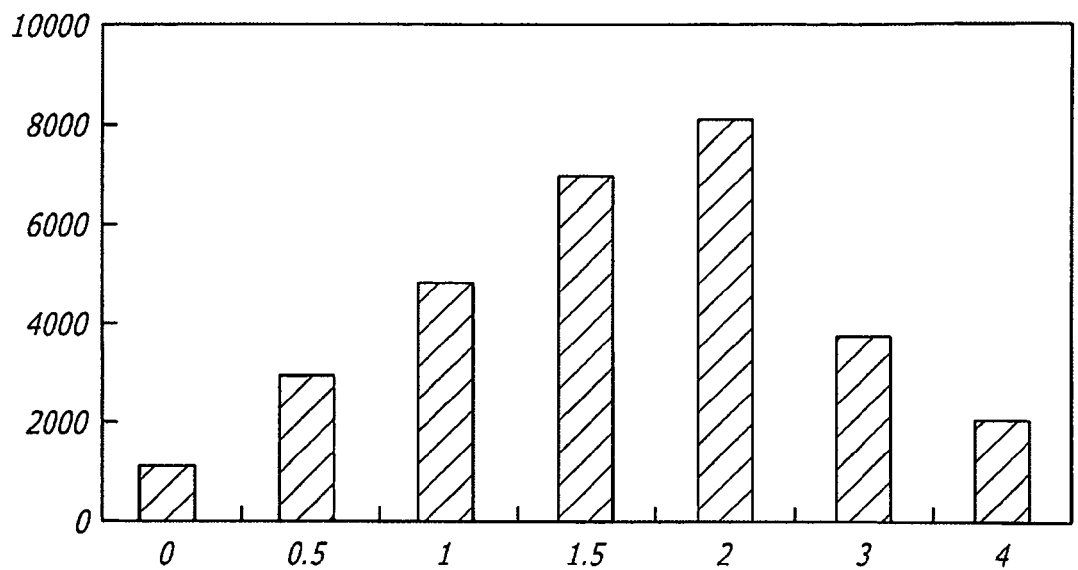
FIG. 10 shows effect of L-His:copper stoichiometry on the reaction.

The overall volume in each vial was 250 microliters containing a solution of 1,8-naphthalimide 1a (0.5 mM), azidofucose 2a (1.0 mM), CUSO$_4$ (1.0 mM), L-histidine (0-3.0 mM) and sodium ascorbate (5.0 mM) in DMSO/water (56% DMSO). The reactions were allowed to stand at room temperature for 24 hours. The catalytic activity was determined by the same method described above (FIG. 10). FIG. 10 shows effect of L-His:copper stoichiometry on the reaction.

Figure 11:
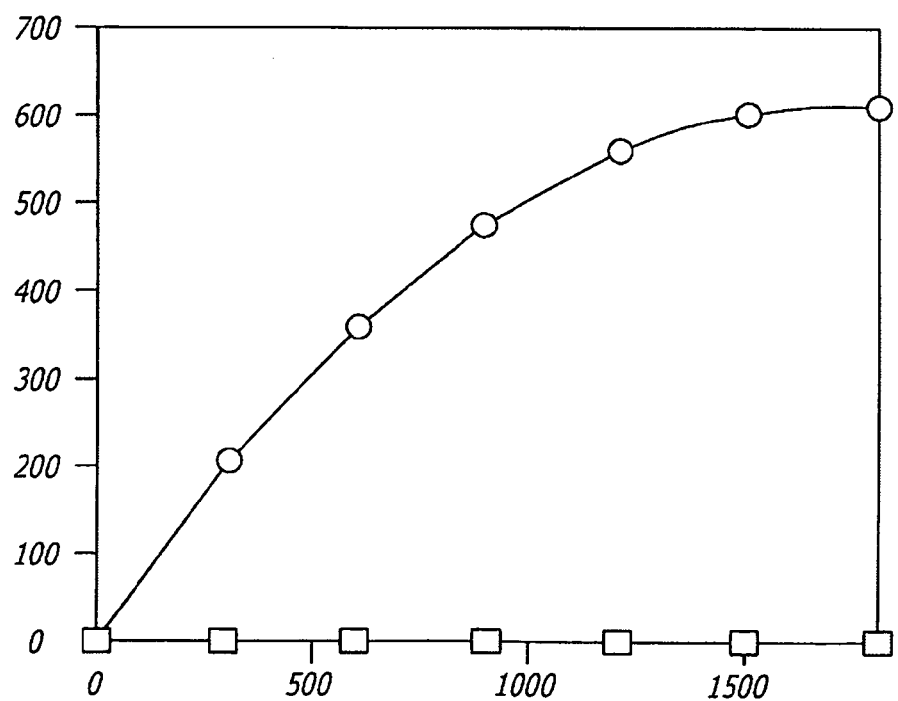
FIG. 11 shows time-course study of histidine-catalyzed reaction at pH 7.2 (50 mM Hepes)

Stoichiometric study of histidine revealed that 2.0 mol equivalent of histidine to copper ion exhibits a maximum effect on the catalysis and any extra amount of ligand hinders the reaction. In this condition, 60% of 1a was converted to the product 10 after 1 h at room temperature and the reaction was completed in less than 6 h. To confirm the effects of L-His on the reaction, we measured the time-course of the reaction by fluorescence spectrometer. Conditions: 1,8-naphthalimide 1a (0.1 mM), azidofucose 2a (1.0 mM), CuSO$_4$ (2.0 mM), L-histidine (0 or 4.0 mM) and sodium ascorbate (100 mM) in 50 mM HEPES buffer (containing 6% DMSO). After mixing all reagents, the fluorescence intensity was measured in 5 min intervals at 37° C. by a fluorescence spectrophotometer (FIG. 11). FIG. 11 shows the time-course study of histidine-catalyzed reaction at pH 7.2 (50 mM Hepes): Filled circle, with L-His; filled square, without L-His. Fluorescence intensities were monitored at λ ex 357 nm and λ em 462 nm.

Synthesis of GDP-fucose Analogs

Example 12

6,7-Deoxy-L-galacto-hept-6-ynopyranosyl phosphate triethylammonium salt (6)

6,7-Deoxy-1,2:3,4-di-O-isopropylidene-alpha-L-galacto-hept-6-ynopyranoside 4 (788 mg, 3.1 mmol) was dissolved in 90% TFA aqueous solution (5 mL) and the solution was stirred at 0° C. for 30 min. The reaction mixture was diluted with water and concentrated in vacuo. The residue was dissolved in pyridine (5 mL) and Ac$_2$O (5 mL), and dimethylaminopyridine (10 mg) was added to the solution. The mixture was stirred at room temperature overnight. The reaction mixture was concentrated and the residue was dissolved in AcOEt, and washed with water, 1N HCl, sat. NaHCO$_3$, and brine. The organic layer was dried over Na$_2$SO$_4$, and evaporated. The residue was purified by flash column chromatography on silica gel (AcOEt/hexane 1:5->1:2) to afford 1,2,3,4-tetra-O-acetyl-6,7-deoxy-L-galacto-hept-6-ynopyranoside as a alpha/beta-anomeric mixture (886 mg, 84%). To a cooled solution of this mixture (200 mg, 0.79 mmol) in CH$_2$Cl$_2$ (5 mL) and Ac$_2$O (0.5 mL) was added dropwise 30% HBr in AcOH (2 mL) at 0° C., and the mixture was stirred for 4 h at room temperature. The reaction mixture was poured onto ice-NaHCO$_3$ aqueous solution and extracted with CH$_2$Cl$_2$. The CH$_2$Cl$_2$ layer was dried over Na$_2$SO$_4$, and evaporated to give the alpha-bromide, which was used without further purification. To a suspension of tetrabutylammonium phosphate (0.4 M in CH$_3$CN, 3 mL, 1.2 mmol) and 4 Å molecular sieves (500 mg) was added a solution of the bromide in dry toluene (2 mL) at 0° C. The mixture was stirred at 0° C. for 30 min, then for 3 h at room temperature. After removal of the solvent, water (5 mL) was added and molecular sieves were filtered off. The filtrate was washed with AcOEt, and then concentrated. 30% NH$_4$OH solution (2 mL) was added to the residue and the mixture was stirred at room temperature for 3 h. The reaction mixture was concentrated, and the residue was acidified with Dowex 50WX8-200 (H$^+$) ion exchange resin. The eluant was neutralized with Et$_3$N and concentrated. The residual oil was applied to a Sephadex G-10 column and eluted with triethylammonium bicarbonate buffer (50 mM, pH 8.0). Fractions containing the products were then purified by a SepPak C-8 cartridge with water. The product fractions were lyophilized to give 6 as a colorless solid (125 mg, 35%); $^1$H-NMR (400 MHz, D$_2$O) δ 1.24 (t, 18H, J=7.2 Hz), 2.91 (d, 1H, J=2.4 Hz), 3.16 (q, 12H, J=7.2 Hz), 3.52 (dd, 1H, J=8.0 and 10.0 Hz), 3.67 (dd, 1H, J=3.2 and 10.0 Hz), 3.94 (d, 1H, J=3.2 Hz), 4.53 (m, 1H), 4.80 (t, J=8.0 Hz); $^{13}$C-NMR (150 MHz, D$_2$O) δ 9.03, 47.38, 67.50, 71.36, 71.47 (d, J=8.0 Hz), 72.43, 76.83, 79.12, 98.48 (d, J=5.7 Hz); $^{31}$P-NMR (160 MHz, D$_2$O) δ 0.72 ESI-TOF-HRMS m/e calculated for $(M-H)^-C_7H_{11}O_8P$ 253.0119; found 253.0124.

Example 13

Guanosine 5'-diphospho-6,7-deoxy-beta-L-galacto-hept-6-ynopyranoside triethylammonium salt (8)

6,7-Deoxy-L-galacto-hept-6-ynopyranosyl phosphate triethyl-ammonium salt 6 (125 mg, 0.27 mmol) and 4-morpholino-N,N'-dicyclohexylcarboxamidinium guanosine 5'-monophosphomorpholidate (300 mg, 0.4 mmol) were dissolved in dry pyridine and coevaporated. To this flask, 1H-tetrazole (60 mg, 0.86 mmol) and dry pyridine (2.5 mL) were added, and the mixture was stirred at room temperature for 3 days. The reaction mixture was diluted with water and extracted with $CH_2Cl_2$, and evaporated. The residual oil was applied to a Sephadex G-10 column and eluted with triethylammonium bicarbonate buffer (50 mM, pH 8.0). Fractions containing the products were then purified by a SepPak C-8 cartridge with water. The product fractions were lyophilized to give 8 as a colorless solid (11 mg, 5%); $^1$H-NMR (600 MHz, $D_2O$) δ 1.28 (t, 18H, J=7.2 Hz), 3.20 (m, 13H), 3.60 (dd, 1H, J=7.8 and 10.2 Hz), 3.70 (dd, 1H, J=3.6 and 10.2 Hz), 3.96 (d, 1H, J=3.0 Hz), 4.22 (m, 1H), 4.35 (m, 1H), 4.52 (m, 1H), 4.54 (m, 1H), 4.81 (t, 1H, J=5.4 Hz), 4.94 (t, 1H, 7.8 Hz), 5.93 (d, 1H, J=6.6 Hz), 8.11 (s, 1H); $^{13}$C-NMR (150 MHz, $D_2O$) δ 9.04, 47.48, 66.18 (d, J=5.4 Hz), 67.61, 71.32, 71.38, 71.43, 72.42, 74.33, 76.82, 84.71 (d, J=9.5 Hz), 87.52, 98.92 (d, J=6.5 Hz), 117.11, 138.53, 152.71, 154.78, 159.84; $^{31}$P-NMR (160 MHz, $D_2O$) δ–10.62 (d, J=20.2 Hz), –12.64 (d, J=20.2 Hz); ESI-TOF-HRMS m/e calculated for $(M-H)^-$ $C_{17}H_{23}N_5O_{15}P_2$ 598.0593; found 598.0607.

Example 14

Guanosine 5'-diphospho-6-azido-beta-L-fucopyranoside triethylammonium salt (9)

6-Azido-beta-L-fucopyranosyl phosphate triethylammonium salt (7)(120 mg, 0.25 mmol) and 4-morpholino-N,N'-dicyclohexylcarboxamidinium guanosine 5'-monophosphomorpholidate (280 mg, 0.39 mmol) were dissolved in dry pyridine and coevaporated. To this flask, 1H-tetrazole (60 mg, 0.86 mmol) and dry pyridine (2.5 mL) were added, and the mixture was stirred at room temperature for 3 days. The reaction mixture was diluted with water and extracted with $CH_2Cl_2$, and evaporated. The residual oil was applied to a Sephadex G-10 column and eluted with triethylammonium bicarbonate buffer (50 mM, pH 8.0). Fractions containing the products were then purified by a SepPak C-8 cartridge with water. The product fractions were lyophilized to give 9 as a colorless solid (75 mg, 36%); $^1$H-NMR (600 MHz, $D_2O$) δ 1.28 (t, 18H, J=7.2 Hz), 3.20 (q, 12H, J=7.2 Hz), 3.46 (dd, 1H, J=6.0 and 12.6 Hz), 3.59 (dd, 1H, J=7.2 and 12.6 Hz), 3.61 (dd, 1H, J=7.8 and 10.2 Hz), 3.68 (dd, 1H, J=3.6 and 10.2 Hz), 3.78 (m, 1H), 3.88 (d, 1H, J=3.6 Hz), 4.21 (m, 1H), 4.35 (m, 1H), 4.53 (dd, 1H, J=3.6 and 5.4 Hz), 4.82 (t, 1H, J=6.0 Hz), 4.96 (t, 1H, 7.8 Hz), 5.93 (d, 1H, J=6.0 Hz), 8.11 (s, 1H); $^{13}$C-NMR (150 MHz, $D_2O$) δ 9.04, 47.49, 51.04, 66.15 (d, J=5.6 Hz), 69.36, 71.35, 71.92 (d, J=8.1 Hz), 72.97, 74.27, 74.45, 84.73 (d, J=9.0 Hz), 87.54, 99.30 (d, J=6.3 Hz), 117.13, 138.57, 152.74, 154.78, 159.84; $^{31}$P-NMR (160 MHz, $D_2O$) δ -10.61 (d, J=20.3 Hz), –12.63 (d, J=20.3 Hz); ESI-TOF-HRMS m/e calculated for $(M-H)^-C_{16}H_{24}N_8O_{15}P_2$ 629.0764; found 629.0791.

Example 15

Typical Glycoconjugate Labeling Experiment

Human alpha$_1$-acid glycoprotein (0.33 mg/mL), pretreated with alpha-fucosidase, was incubated with human alpha-1,3-fucosyltransferase V (100 mU/mL) in MOPS buffer (50 mM, pH 7.2) containing 150 mM NaCl, 10 mM $MnCl_2$, 4 mM ATP, 0.2 mM GDP-fucose analog (8-10). After incubation at 37° C. for 8 h, additional GDP-fucose derivative (final 0.4 mM) was added and the reaction mixture was incubated at 37° C. for 12 h. The reaction mixture was passed through a NAP-5 column (Amersham) equilibrated in water to remove remaining GDP-fucose analogs, and the protein fractions were lyophilized. The glycoproteins was then subjected to the cycloaddition labeling reaction.

The fucosylated glycoconjugate was dissolved in HEPES buffer (50 mM, pH 7.6), and added to a solution containing $CuSO_4$ (0.2 mM), 1.0 mM sodium ascorbate, the tris(triazolyl)amine ligand (20) (0.2 mM, stock in DMSO), and the appropriate naphthalimide ligation probe 1a or 1b (0.1 mM, stock in DMSO, final concentration of DMSO; 10%)). After 1 h at room temperature, the mixture was passed through NAP-5 column in water and lyophilized, and analyzed by SDS-PAGE.

Example 16

Analysis of Decomposition of Probe 1b by LC-MS

Figure 12:
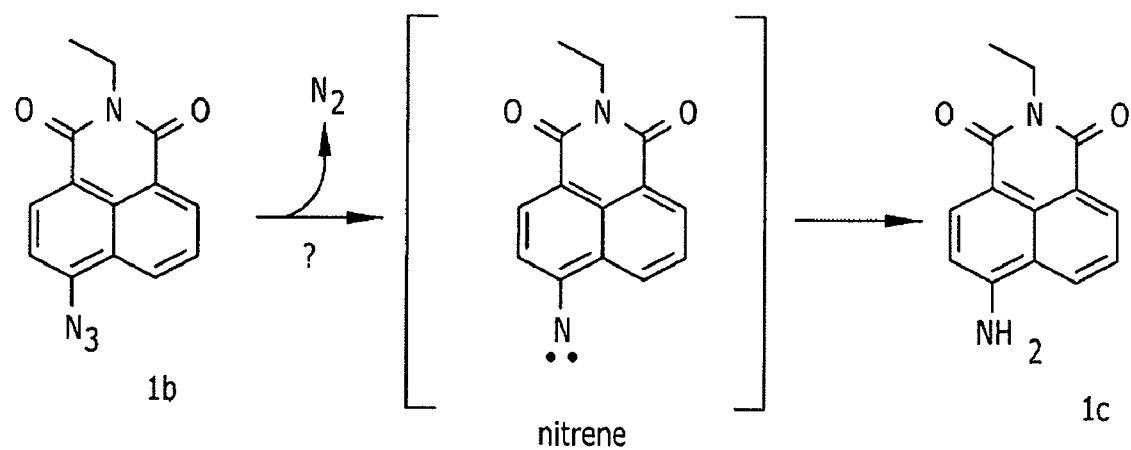
FIG. 12 shows decomposition of compound 1b.

During the labeling reaction, the excess probe 1b seemed to decompose into a strongly fluorescent product which resulted in a slight background signal. Bicyclic aromatic azides are known to easily decompose by thermolysis or photolysis through a highly reactive nitrene intermediate (FIG. 12). FIG. 12 shows decomposition of compound 1b.

Figure 13C:
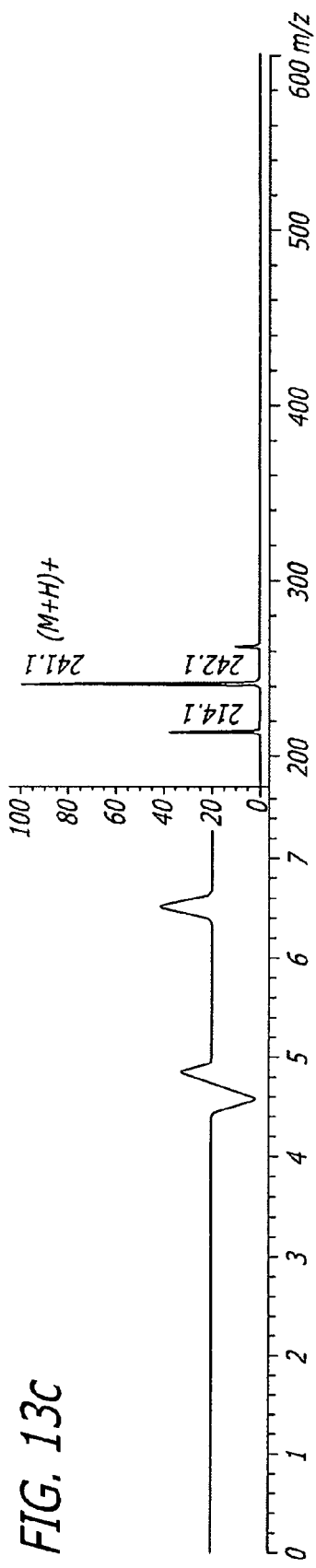
FIG. 13 shows LC-MS analysis of decomposition of 1b.
Figure 13D:
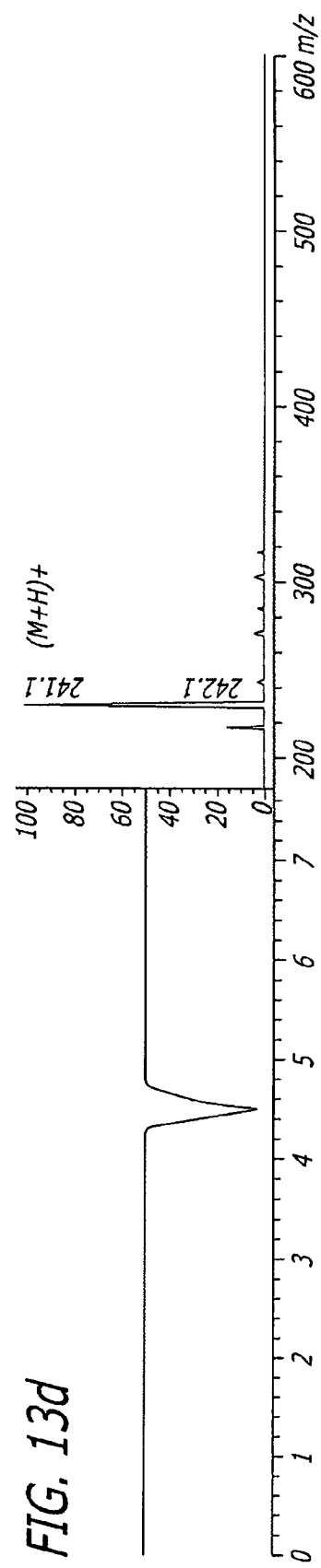

Thus we analyzed the decomposition of 1b using LC-MS (FIG. 13). FIG. 13 shows LC-MS analysis of decomposition of 1b. The compounds were monitored at 350 nm by using an Agilent SB C8 50×4.6 mm column. (a) 1b. (b) Cycloaddition reaction with 7. (c) After 12 h incubation without 7. (d) The synthesized 4-amino derivative 1c (1). See typical experimental procedure of cycloaddition for the reaction conditions.

In the presence of 6-alkyne fucose 2b, probe 1b was completely converted into the product 3b. However, without 6-alkyne fucose 3b, probe 1b decomposed into a fluorescent compound with a molecular weight corresponding to the 4-amino derivative 1c ($[M+H]^+$ 241; ca. 80% conversion after 12 h incubation at room temperature). The decomposed compound showed a green fluorescence with a maximum emission at 534 nm when excited at 417 nm, which was agreement with the reported data of 1c.

Example 17

Analysis of Fluorescent Labeling at the Cell Surface by Flow Cytometry

Jurkat cells were cultured in RPMI 1640 (Invitrogen, Carlsbad, Calif.) supplemented with 10% FCS and peracetylated fucose 11 or azidofucose 12 (200 mM) at the density of 2×10$^5$ cells/mL for 3 days, in the presence or absence of tunicamycin (5 mg/mL). After washing with 0.1% FCS/PBS, 10$^6$ cells were resuspended in 100 mL of a reaction solution (0.1 mM probe 1a, or biotinylated alkyne 13, 0.2 mM tris-triazoleamine catalyst, and 0.1 mM CuBr in PBS) at room temperature for 30 min, followed by wash with 0.1% FCS/PBS. For the biotinylation experiment, cells were subsequently stained with 0.25 mg of UltraAvidin™-Fluorescein (Leinco Technologies, St. Louis, Mo.) in 50 mL of staining buffer (1% FCS and 0.1% $NaN_3$ in PBS) for 30 min at 4° C., followed by three washes with staining buffer. The fluorescence intensity was detected and acquired by BD LSR II (BD Biosciences, San Jose, Calif.) and FACSDiva software (BD Biosciences). 20,000 events were collected in each sample. Data analysis was performed with CellQuestPro software (BD Biosciences). For detection of the fluorescent adduct with probe 1a, a 351 nm UV laser was used for excitation and emission was detected by a 440/40 bandpass filter.

Example 18

Fluorescence Microscopy and Imaging

Human hepatocellular carcinoma cell line, Hep3B cells (ATCC), were cultured in Opti-MEM (Invitrogen) supplemented with 0.1% FCS and treated with natural fucose or peracetylated azidofucose 12 (200 micromolar) for 3 days. Then, the cells were transferred to a coverslip glass slide, and cultured overnight in the same medium. The cells were fixed by acetone and subjected to the appropriate labeling reaction. For labeling reaction, fixed cells were incubated with 0.2 mM probe 1a, 2.0 mM tris-triazoleamine catalyst, 1.0 mM $CUSO_4$, 2.0 mM sodium ascorbate in PBS at room temperature overnight. After labeling, cells were washed with PBS, and fluorescence images were obtained using Axiovert 200M (Carl Zeiss, Inc.). For counter staining of Golgi compartments, the fixed cells were stained using Alexa Fluor® 594 conjugated WGA lectin (Molecular Probes), and each fluorescent dye was imaged using Bio-Rad (Zeiss) Radiance 2100 Rainbow laser scanning confocal microscopy system.

Example 19

Synthesis of Biotinylated Alkyne 13

A mixture of D-(+)-biotin (100 mg, 0.41 mmol), propargylamine (45 mg, 0.82 mmol), O-(Benzotriazol-1-yl)-N,N,N',N'-tetramethyluronium hexafluorophosphate (311 mg, 0.82 mmol) and N,N-diisopropylethylamine (106 mg, 0.82 mmol) in DMF (5 mL) was stirred at room temperature for 2 h. The reaction mixture was concentrated in vacuo, and the residue was purified by flash column chromatography ($CHCl_3$/MeOH 10:1) to give the amide 13. Recrystallization from $CHCl_3$ gave 13 as a colorless solids (100 mg, 87%); $^1$H-NMR (500 MHz, DMSO-$d_6$) δ 1.31-1.39 (m, 2H), 1.51-1.59 (m, 3H), 1.64-1.70 (m, 1H), 2.14 (t, 2H, J=7.5 Hz), 2.64 (d, 1H, J=12.0 Hz), 2.88 (dd, 1H, J=5.0 and 12.0 Hz), 3.13 (t, 1H, J=2.5 Hz), 3.15-3.18 (m, 1H), 3.89 (q, 1H, J=2.5 Hz), 4.17-4.21 (m, 1H), 4.35-4.38 (m, 1H), 6.41 (s, 1H), 6.47 (s, 1H), 8.27 (m, 1H); ESI-TOF-HRMS m/e calculated for (M+H)$^+$ $C_{13}H_{20}N_3O_2S$ 282.1271; found 282.1276.

While various embodiments of the present disclosure have been described in detail, it is apparent that modifications and adaptations of those embodiments will occur to those skilled in the art. However, it is to be expressly understood that such modifications and adaptations are within the spirit and scope of the present disclosure.

The invention claimed is:

1. A composition comprising:
an alkynyl-derivatized fucose-GDP analog having an alkyl group at the position 6 of the fucose-GDP for binding a probe for detecting a glycoconjugate.

2. The composition of claim 1, wherein the probe emits a fluorescent signal.

3. The composition of claim 1, wherein the probe is contacted by a secondary probe, wherein the secondary probe emits a detectable signal.

4. The composition of claim 3, wherein the secondary probe emits a fluorescent signal.

5. A composition comprising:
an alkynyl-derivatized fucose-GDP analog having an azido group at the position 6 of the fucose-GDP for binding a probe for detecting a glycoconjugate.

6. The composition of claim 5, wherein the probe emits a fluorescent signal.

7. The composition of claim 5, wherein the probe is contacted by a secondary probe, wherein the secondary probe emits a detectable signal.

8. The composition of claim 7, wherein the secondary probe emits a fluorescent signal.

9. The composition of claim 5, wherein the composition is formed from an azido-derivatized fucose analog, wherein the azido-derivatized fucose is converted to azido-derivatized fucose-GDP analog by a fucosyltransferase.

* * * * *